(12) United States Patent
Bansal

(10) Patent No.: US 9,040,507 B2
(45) Date of Patent: May 26, 2015

(54) METHOD FOR TREATING INFLAMMATORY CONDITIONS

(75) Inventor: Rekha Bansal, Twinsburg, OH (US)

(73) Assignee: Novelmed Therapeutics, Inc., Cleveland, OH (US)

(*) Notice: Subject to any disclaimer, the term of this patent is extended or adjusted under 35 U.S.C. 154(b) by 606 days.

(21) Appl. No.: 12/995,885

(22) PCT Filed: Jun. 2, 2009

(86) PCT No.: PCT/US2009/045969
§ 371 (c)(1),
(2), (4) Date: Dec. 2, 2010

(87) PCT Pub. No.: WO2009/149081
PCT Pub. Date: Dec. 10, 2009

(65) Prior Publication Data
US 2011/0082126 A1    Apr. 7, 2011

Related U.S. Application Data

(60) Provisional application No. 61/057,941, filed on Jun. 2, 2008.

(51) Int. Cl.
| | |
|---|---|
| A61K 31/565 | (2006.01) |
| A61K 31/138 | (2006.01) |
| A61K 31/137 | (2006.01) |
| A61K 31/085 | (2006.01) |
| A61P 37/00 | (2006.01) |
| A61K 31/01 | (2006.01) |
| A61K 31/015 | (2006.01) |

(52) U.S. Cl.
CPC ............ *A61K 31/01* (2013.01); *A61K 31/015* (2013.01)

(58) Field of Classification Search
USPC ........................................ 514/171, 651, 720
See application file for complete search history.

(56) References Cited

U.S. PATENT DOCUMENTS

| | | |
|---|---|---|
| 3,852,324 A | 12/1974 | Wright |
| 5,807,830 A | 9/1998 | Morozov et al. |
| 5,807,899 A | 9/1998 | Bohlmann et al. |
| 5,869,660 A | 2/1999 | Adams et al. |
| 6,528,681 B2 | 3/2003 | Kaltenbach, III et al. |
| 2007/0110685 A1 | 5/2007 | Auspitz et al. |

FOREIGN PATENT DOCUMENTS

| | | |
|---|---|---|
| WO | WO 02/057219 A1 | 7/2002 |
| WO | WO 03/066806 A2 | 8/2003 |
| WO | WO 2005/123193 A2 | 12/2005 |
| WO | WO 2007/084542 A2 | 7/2007 |

OTHER PUBLICATIONS

Filler (Tumor necrosis Factor Inhibition and Invasive Fungal Infections, Clinic of Infectious Disease, (2005) 41 (Supplement 3): S208-S212).*
Lackner (Bifonazole, A review of its antimicrobial activity and therapeutic use in superficial mycoses, Drugs, 1989 Aug: 38(2): abstract only.*

* cited by examiner

*Primary Examiner* — Kathrien Cruz
(74) *Attorney, Agent, or Firm* — Tarolli, Sundheim, Covell & Tummino LLP

(57) ABSTRACT

A method for treating an autoimmune disease in a subject includes administering to the subject a therapeutically effective amount of an agent comprising an imidazole, an estrogen receptor agonist, or pharmaceutically acceptable salts thereof.

11 Claims, 46 Drawing Sheets

The Effect of TC5 on Ankle Damage in a Prophylactic Model of Rat AIA (IP Dosing)

The Effect of TC5 on Joint Histology in a Prophylactic Model of Rat AIA (IP Dosing)

The Effect of TC5 on Ankle Damage in a Prophylactic Model of Rat AIA (Oral Dosing)

The Effect of TC10 on Ankle Damage in a Prophylactic Model of Rat AIA (IP Dosing)

The Effect of TC10 on Ankle Histology in a Prophylactic Model of Rat AIA (IP Dosing)

The Effect of TC10 on Joint Damage in a Prophylactic Model of Rat AIA (IP Dosing, Male Rats)

The Effect of TC10 on Joint Damage in a Prophylactic Model of
Rat AIA (IP Dosing, Male Rats)

The Effect of TC10 on Joint Damage in a Prophylactic Model of Rat AIA (Oral Dosing, Male Rats)

The Effect of TC10 on Joint Damage in a Prophylactic Model of Rat AIA (Oral Dosing, Male Rats)

METHOD FOR TREATING INFLAMMATORY CONDITIONS

RELATED APPLICATION

This application corresponds to PCT/US2009/045969, filed Jun. 2, 2009, which claims the benefit of U.S. Provisional Application No. 61/057,941, filed Jun. 2, 2008, the subject matter, which is herein incorporated by reference in its entirety.

TECHNICAL FIELD

The present invention relates generally to a method for treating inflammatory conditions, and more particularly to a method for treating an inflammatory condition in a subject by administering at least one of an imidazole, a synthetic estrogen, or a combination thereof to a subject in need thereof.

BACKGROUND OF THE INVENTION

One percent of humans worldwide are afflicted with rheumatoid arthritis (RA), a relentless, progressive disease causing severe swelling, pain, and eventual deformity and destruction of joints. According to the Arthritis Foundation, RA currently affects over two million Americans, of which women are three times more likely to be afflicted. RA is characterized by inflammation of the lining of the joints and/or other internal organs, and the presence of elevated numbers of lymphocytes and high levels of proinflammatory cytokines.

For many years, corticosteroids have been used extensively as a first line treatment of RA. Unfortunately, corticosteroid therapy is often accompanied by numerous side effects, including bone loss, increased susceptibility to infection, osteoporosis, and peptic ulcers. Additionally, weaning patients from corticosteroids can be difficult and relapses of articular degeneration are frequent once the steroid is discontinued. These steroidal compounds are potent inhibitors of tumor necrosis factor (TNF). Therefore, all TNF inhibitors are not desired clinical candidates.

SUMMARY OF THE INVENTION

The present invention relates to a method for treating an inflammatory condition in a subject. The method includes administering to the subject a therapeutically effective amount of an agent comprising at least one imidazole or estrogen receptor agonist having a formula selected from the group consisting of:

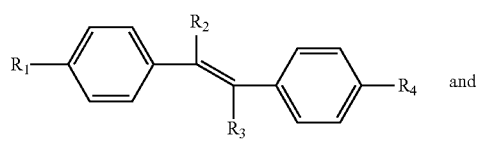

and

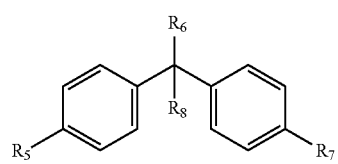

wherein $R_1$, $R_2$, $R_3$, $R_4$, $R_5$, $R_6$, $R_7$, and $R_8$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halogen, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof or a pharmaceutically acceptable salt thereof, and wherein at least one of $R_2$, $R_3$, $R_6$, or $R_8$ is a hydrogen, a halogen, an imidazole, a substituted imidazole, an aryl, or a substituted aryl.

In an aspect of the invention, the agent can be an estrogen receptor agonist having the formula of:

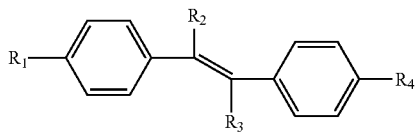

and wherein $R_1$, $R_2$, $R_3$, and $R_4$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halogen, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—$NO_2$), nitroso (—NO), sulfo (—$SO_2$—OH), sulfonato (—$SO_2$—O), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—$PO_2$), phosphino (—$PH_2$), and combinations thereof or a pharmaceutically acceptable salt thereof. In another aspect of the invention, at least one of $R_2$ or $R_3$ is selected from group consisting of a hydrogen, a halogen, an aryl, or a substituted aryl.

In a further aspect of the invention, the estrogen receptor agonist has the formula:

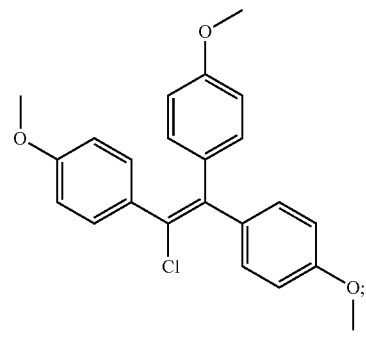

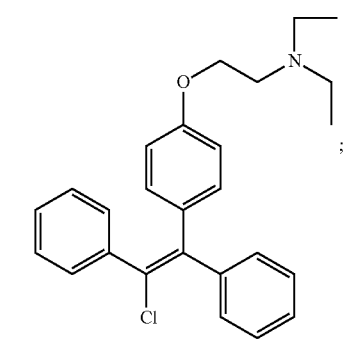

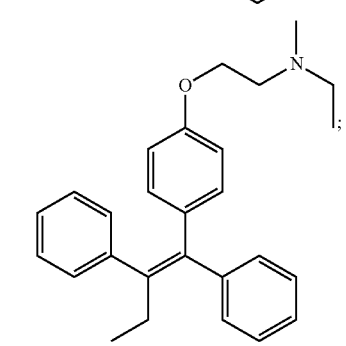

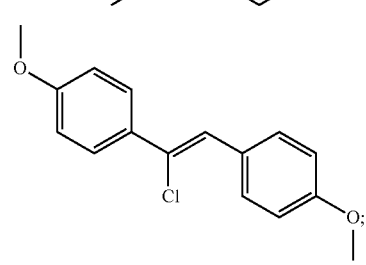

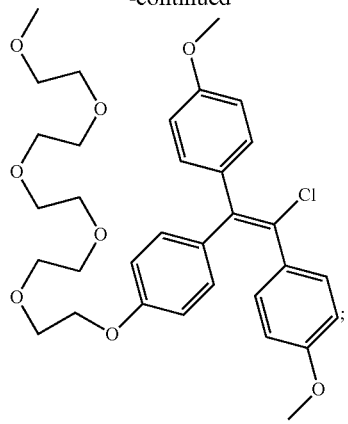

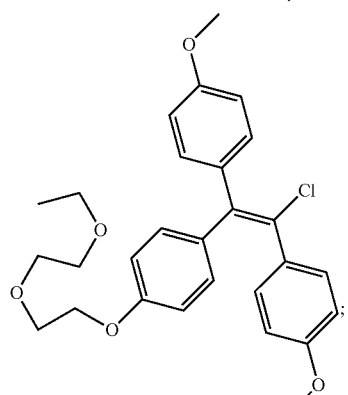

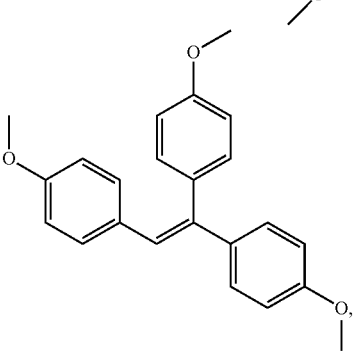

and pharmaceutically acceptable salts thereof.

In a still further aspect of the invention, the agent is an imidazole. One example of an imidazole is 1-[phenyl(4-phenylphenyl)methyl]-1H-imidazole 1-[phenyl(4-phenylphenyl)methyl]-1H-imidazole or a pharmaceutically acceptable salt thereof.

In an aspect of the invention, the inflammatory condition can include an autoimmune disease that is selected from the group consisting of osteoarthritis, rheumatoid arthritis, septic arthritis, gout, pseudogout, juvenile idiopathic arthritis, Still's disease, Ankylosing spondylitis, lupus erythematosus, sarcoidosis, Henoch-Schönlein purpura, psoriatic arthritis, reactive arthritis, haemochromatosis, hepatitis, Wegener's granulomatosis, Lyme disease, familial mediterranean fever, hyperimmunoglobulinemia D with recurrent fever, TNF receptor associated periodic syndrome, inflammatory bowel disease, and diseases that can mimic arthritis.

The present invention also relates to a method for treating an autoimmune disease in a subject that includes administering to the subject a therapeutically effective amount of an anti-TNF or an anti-IL-1 compound; and at least one imidazole or estrogen receptor agonist having a formula selected from the group consisting of:

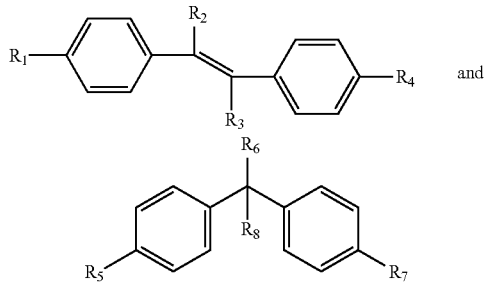

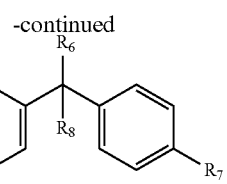

wherein $R_1$, $R_2$, $R_3$, $R_4$, $R_5$, $R_6$, $R_7$, and $R_8$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halogen, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O⁻), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O⁻)$_2$), phosphinato (—P(O)(O⁻)), phospho (—PO$_2$), phosphino (—PH$_2$), and combinations thereof or a pharmaceutically acceptable salt thereof, and wherein at least one of $R_2$, $R_3$, $R_6$, or $R_8$ is a hydrogen, a halogen, an imidazole, a substituted imidazole, an aryl, or a substituted aryl.

In an aspect of the invention, the amount of component (a) can be a single dose prophylactic treatment followed by a dose of component (b). In a further aspect, the amount of component (a) is a sub-therapeutic dose.

The present invention further relates to a method for treating rheumatoid arthritis in a subject that includes administering to the subject a therapeutically effective amount of an agent comprising at least one imidazole or estrogen receptor agonist having a formula selected from the group consisting of:

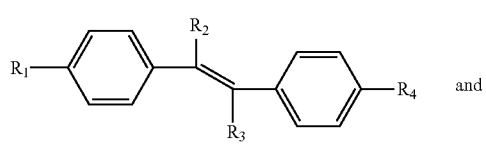

wherein $R_1$, $R_2$, $R_3$, $R_4$, $R_5$, $R_6$, $R_7$, and $R_8$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halogen, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O⁻), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O⁻)$_2$), phosphinato (—P(O)(O⁻)), phospho (—PO$_2$), phosphino (—PH$_2$), and combinations thereof or a pharmaceutically acceptable salt thereof, and wherein at least one of $R_2$, $R_3$, $R_6$, or $R_8$ is a hydrogen, a halogen, an imidazole, a substituted imidazole, an aryl, or a substituted aryl.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
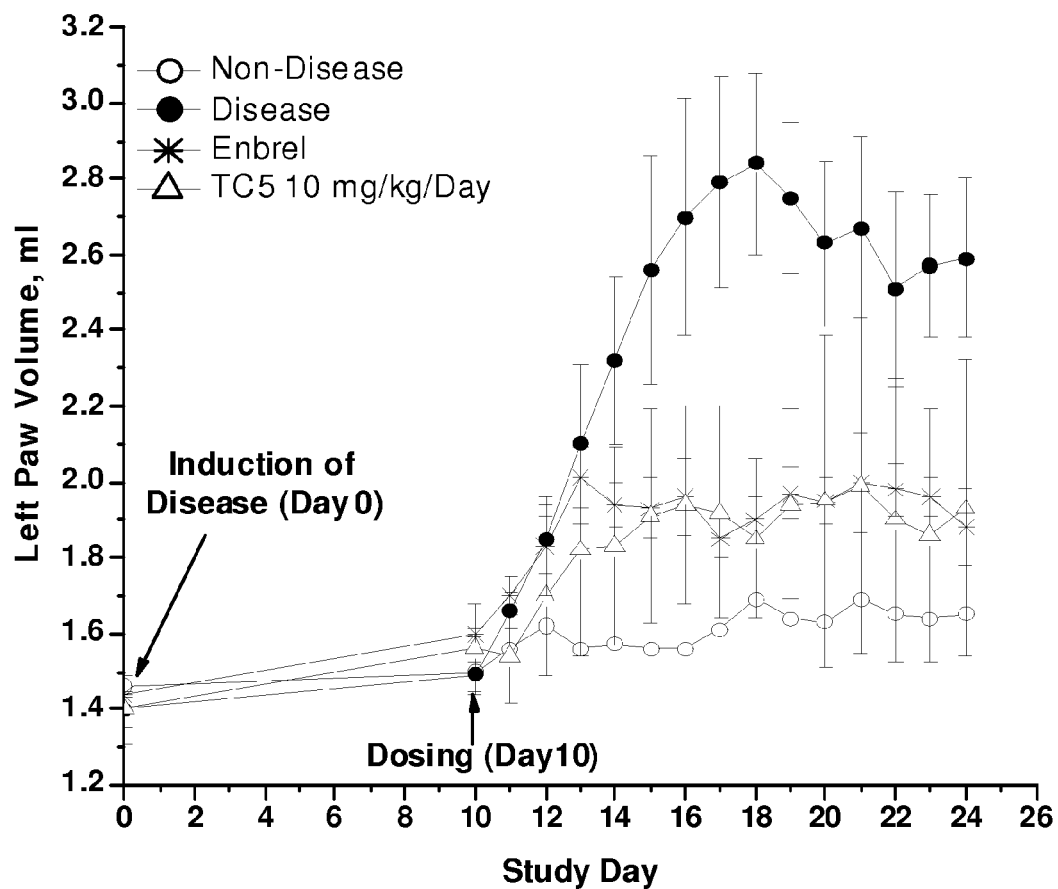
FIG. 1 is a graph showing the effect of bifonazole (hereinafter, "TC5") on left paw inflammation in a prophylactic model of rat antigen-induced arthritis (AIA). TC5 was administered intraperitoneally at 10 mg/kg/day. The administration was given prophylactically at day 10 to demonstrate prevention of arthritis in rats. Development of arthritis usually takes 14 days to progress. TC5 was administered at day 10 and inhibition of arthritis was measured on left paw inflammation.

For convenience, certain terms employed in the specification, examples, and appended claims are collected here. Unless defined otherwise, all technical and scientific terms used herein have the same meaning as commonly understood by one of ordinary skill in the art to which this invention belongs.

The phrase "having the formula" or "having the structure" is not intended to be limiting and is used in the same way that the term "comprising" is commonly used.

The term "alkyl" refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Substituents identified as "$C_1$-$C_6$ alkyl" or "lower alkyl" can contain 1 to 3 carbon atoms, and more particularly such substituents can contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "C1-C6 alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano(—CN), isocyano (—N+C—), cyanato (—O—CN), isocyanato (—ON+C—), isothiocyanato (—S—CN), azido (—N=N+=N—), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O—)$_2$), phosphinato (—P(O)(O—)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

When referring to a compound of the invention, applicants intend the term "compound" to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

Some of the compounds disclosed herein may contain one or more asymmetric centers and may thus give rise to enantiomers, diastereomers, and other stereoisomeric forms. The present invention is also meant to encompass racemic mixtures, resolved forms and mixtures thereof, as well as the individual enantiomers that may be separated according to methods that are well know to those of ordinary skill in the art. When the compounds described herein contain olefinic double bonds or other centers of geometric asymmetry, and unless specified otherwise, it is intended to include both E and Z geometric isomers.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "asymmetric center" or "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

In the context of the present invention, the term "subject" refers to any warm-blooded organism including, but not limited to, human beings, pigs, rats, mice, dogs, goats, sheep, horses, monkeys, apes, rabbits, cattle, etc.

As used herein, the terms "treatment," "treating," or "treat" refer to any treatment of an inflammatory condition or TNF-α-mediated condition in a subject including, but not limited to, preventing the condition from developing, inhibiting development of the condition, arresting development of clinical symptoms associated with the condition, and/or relieving the symptoms associated with the condition.

As used herein, the term "effective amount" refers to a dosage of at least one pharmaceutical agent that is sufficient to provide treatment for an autoimmune disease, disorder, or condition. The effective amount can vary depending on the subject, the condition being treated, and the treatment being affected.

As used herein, the term "therapeutically effective amount" refers to that amount of at least one pharmaceutical agent that results in amelioration of symptoms or a prolongation of survival in a subject. A therapeutically relevant effect relieves to some extent one or more symptoms of an inflammatory condition, or returns to normal, either partially or completely, one or more physiological or biochemical parameters associated with or causative of the condition.

The term "pharmaceutical composition" refers to a preparation of one or more of the pharmaceutical agents described herein with other chemical components, such as physiologically suitable carriers and excipients. The purpose of a pharmaceutical composition is to facilitate administration of a pharmaceutical agent to a subject.

As used herein, the term "modulate" refers to affecting a change in the level, activity, amount or other characteristic of a desired target, such as a molecule or cell.

As used herein, the term "inflammatory condition" refers to a condition or disease characterized by activation of the immune system to abnormal levels that leads to the disease. An inflammatory condition can include a state in which there is a response to tissue damage, cell injury, an antigen, an infectious disease, and/or some unknown cause. Symptoms of inflammation may include, but are not limited to, cell infiltration and tissue swelling.

The present invention relates generally to a method for treating inflammatory conditions, such as rheumatoid diseases, autoimmune conditions, and conditions associated with bone loss, joint destruction and inflammation by administering to a subject in need thereof a therapeutically effective amount of an agent comprising at least one of an imidazole, estrogen receptor agonist, or a combination thereof. It was found that imidiazoles, such as 1-[phenyl(4-phenylphenyl) methyl]-1H-imidazole (bifonazole) can reduce paw inflammation (FIGS. 1-2) and ankle damage (FIGS. 4-5) in a rat antigen-induced arthritis (AIA) model of arthritis; (2) imidiazoles, such as bifonazole, can reduce paw inflammation (FIG. 19) in a mouse collagen-induced arthritis (CIA) model of arthritis; (3) estrogen receptor agonists can reduce paw inflammation (FIG. 20) and ankle damage (FIGS. 23-24) in a rat AIA model of arthritis; and (4) estrogen receptor agonists, such as 1,1',1"-(2-chloroethene-1,1,2-triyl)tris(4-methoxybenzene) (chlorotrianisene) and (Z)-2-[4-(1,2-diphenylbut-1-enyl)phenoxy]-N,N-dimethyl-ethanamine (tamoxifen), can reduce paw inflammation (FIGS. 41 and 42) in a mouse CIA model of arthritis. Moreover, the imidazoles and estrogen receptor agonists of the present invention can prevent activation and infiltration of neutrophils and monocytes, prevent cartilage degradation and bone damage, prevent "NF kappa B" pathway to cellular damage without preventing TNF alpha production in whole blood cultures. Based on these discoveries, the present invention provides a method for treating inflammatory conditions and autoimmune diseases, such as rheumatoid arthritis in a subject.

In one aspect of the invention, the imidazole or estrogen receptor agonist can have a formula selected from the group consisting of:

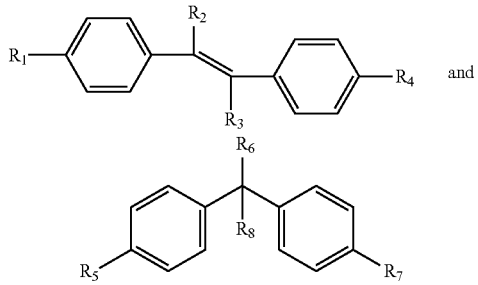

and wherein $R_1$, $R_2$, $R_3$, $R_4$, $R_5$, $R_6$, $R_7$, and $R_8$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halogen, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)-β-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof or a pharmaceutically acceptable salt thereof, and wherein at least one of $R_2$, $R_3$, $R_6$, or $R_8$ is a hydrogen, a halogen, an imidazole, a substituted imidazole, an aryl, or a substituted aryl.

In a further aspect of the invention, the agent can be an estrogen receptor agonist having the formula:

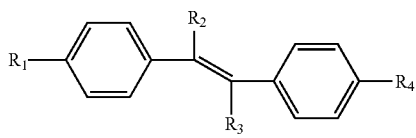

wherein at least one of $R_2$ or $R_3$ is selected from group consisting of a hydrogen, a halogen, an aryl, or a substituted aryl.

In yet another aspect of the invention, the estrogen receptor agonist can have the formula:

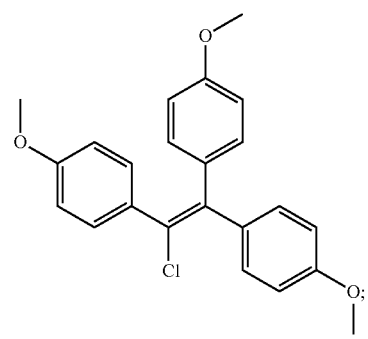 [SMILES: COc1ccc(C(Cl)=C(c2ccc(OC)cc2)c2ccc(OC)cc2)cc1]

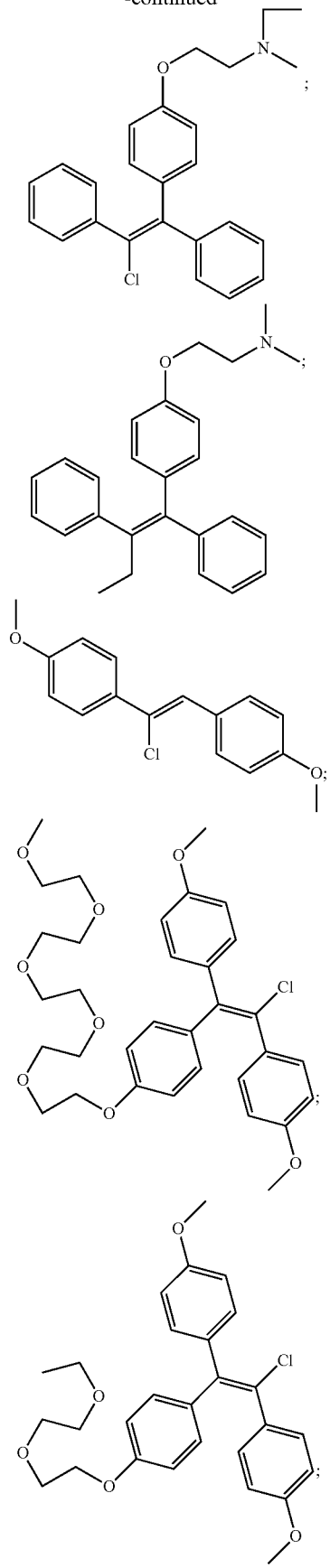

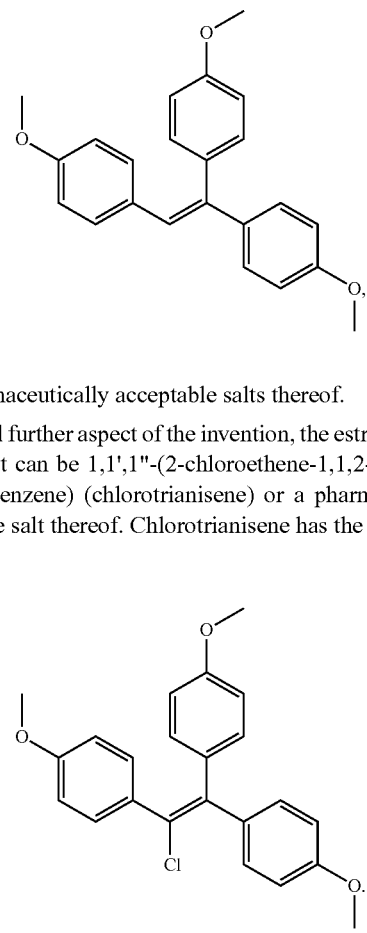

and pharmaceutically acceptable salts thereof.

In a still further aspect of the invention, the estrogen receptor agonist can be 1,1',1''-(2-chloroethene-1,1,2-triyl)tris(4-methoxybenzene) (chlorotrianisene) or a pharmaceutically acceptable salt thereof. Chlorotrianisene has the formula:

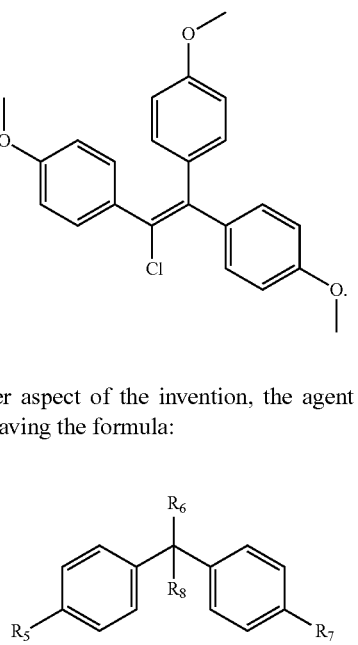

In another aspect of the invention, the agent can be an imidazole having the formula:

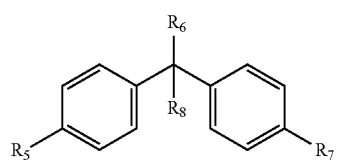

wherein at least one $R_6$ or $R_8$ is an imidazole or substituted imidazole.

Examples of imidazoles having this formula include antifungals imidiazoles, such as 1-[phenyl(4-phenylphenyl)methyl]-1H-imidazole (bifonazole) and 1-[(2-chlorophenyl)(diphenyl)methyl]-1H-imidazole (clotrimazole), which have the formulas of:

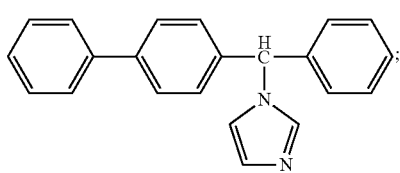

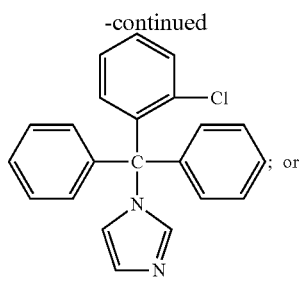

pharmaceutically acceptable salts thereof.

In another aspect of the present invention, the agent can be formulated as a pharmaceutical composition using techniques routinely used in the art. Such a composition can comprise, for example, a therapeutically effective amount of the at least one pharmaceutical agent and a pharmaceutically acceptable carrier. A pharmaceutical composition can be formulated to release at least one pharmaceutical agent substantially immediately upon administration to a subject or, alternatively, at any predetermined time period after administration using, for example, controlled release formulations. Pharmaceutical compositions can be formulated according to conventional pharmaceutical practice (see, e.g., Remington: The Science and Practice of Pharmacy, (20th ed.) ed. A. R. Gennaro, 2000, Lippincott Williams & Wilkins, Philadelphia, Pa. and Encyclopedia of Pharmaceutical Technology, eds. J. Swarbrick and J. C. Boylan, 1988-2002, Marcel Dekker, New York).

Administration of pharmaceutical agents in controlled release formulations may be useful where the at least one pharmaceutical agent, either alone or in combination, has: (1) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose (LD50) to median effective dose (ED50)); (2) a narrow absorption window in the gastro-intestinal tract; or (3) a short biological half-life, so that frequent dosing during the day is required in order to sustain the plasma level at a therapeutic level.

The term "pharmaceutically acceptable" means approved by a regulatory agent of the Federal or state government, or listed in the U.S. Pharmacopeia or other generally recognized pharmacopeia for use in animals, such as humans. The term "carrier" refers to a diluent, adjuvant, excipient, stabilizer, or vehicle with which the agent is formulated for administration. Pharmaceutical carriers can be sterile liquids, such as water and oils, including those of petroleum, animal, vegetable or synthetic origin, such as peanut oil, soybean oil, mineral oil, sesame oil, and the like. Water is a typical carrier when the pharmaceutical composition is administered intravenously. Saline solutions and aqueous dextrose and glycerol solutions can be employed as liquid carriers, particularly for injectable solutions.

Suitable pharmaceutical excipients can include starch, glucose, lactose, sucrose, gelatin, malt, rich, flour, chalk, silica gel, sodium stearate, glycerol monostearate, talc, sodium chloride, dried skim milk, glycerol, propylene, glycol, water, ethanol, and the like. The pharmaceutical composition, if desired, can also contain minor amounts of wetting or emulsifying agents, or pH buffering agents. Pharmaceutical compositions can take the form of solutions, suspensions, emulsions, tablets, pills, capsules, powders, sustained-release formulations, and the like. The pharmaceutical composition can also be formulated as a suppository, with traditional binders and carriers such as triglycerides.

Oral formulations can include standard carriers such as pharmaceutical grades of mannitol, lactose, starch, magnesium stearate, sodium saccharine, cellulose, magnesium carbonate, and the like. Such compositions may contain a therapeutically effective amount of bifonazole or chlorotrianisene, for example, typically in purified form, together with a suitable amount of carrier so as to provide a formulation proper for administration to a subject. Generally, the formulation should suit the mode of administration.

A pharmaceutical agent of the present invention may also be formulated in accordance with routine procedures as a pharmaceutical composition adapted for intravenous administration to human beings. Typically, pharmaceutical compositions for intravenous administration are solutions in sterile isotonic aqueous buffer. Where necessary, the pharmaceutical composition can also include a solubilizing agent. Generally, the ingredients are supplied either separately or mixed together in unit dosage form as, for example, dry lyophilized powder or water-free concentrate in a hermetically sealed container (e.g., an ampoule or sachette) indicating the quantity of the active agent. Where the pharmaceutical composition is to be administered by infusion, the pharmaceutical composition can be dispensed with an infusion bottle containing sterile pharmaceutical grade water or saline. Where the pharmaceutical composition is administered by injection, an ampoule of sterile water for injection or saline can be provided so that the ingredients can be mixed prior to administration.

It will be appreciated that other routes of administration are also possible, including, for example, oral, intraperitoneal, parenteral, subcutaneous, transdermal, sublingual, nasal, opthalmic, intramuscular, pulmonary (i.e., inhalation), topical, intraarticular, rectal and vaginal routes.

The pharmaceutical agents of the present invention can be formulated as neutral or salt forms. Pharmaceutically acceptable salts can include those formed with free amino groups such as those derived from hydrochloric, phosphoric, acetic, oxalic, tartaric acids, and the like. Other pharmaceutically acceptable salts can include those formed with free carboxyl groups, such as those derived from sodium, potassium, ammonium, calcium, ferric hydroxides, isopropylamine, triethylamine, 2-ethylamino ethanol, histidine, procaine, and the like.

The amount of the pharmaceutical agent which will be effective in the treatment of a particular condition or disease will depend on the route of administration and the seriousness of the condition or disease, and should be decided according to the judgment of a qualified medical professional. In vitro assays can optionally be employed to help identify optimal dosage ranges. Effective doses may also be extrapolated from dose response curves derived from in vitro or animal model test systems, such as those described below.

The dosage of a pharmaceutical composition may depend on several factors including, but not limited to, the administration route, the condition or disease to be treated, the severity of the condition or disease, whether the condition or disease is to be treated or prevented, and the age, weight, and health of the subject to be treated. Additionally, pharmacogenomic information (e.g., the effect of genotype on the pharmacokinetic, pharmacodynamic or efficacy profile of a pharmaceutical agent, etc.) about a particular subject may affect the dosage used. When systemically administered to a human, for example, a pharmaceutical agent comprising an anti-fungal azole (e.g., bifonazole) can be administered or present in pharmaceutical composition at a dosage of about 1 µg to about 200 mg per day, about 5 mg to about 750 mg per day, or about 1 mg to about 1000 mg per day.

In another aspect of the present invention, the inflammatory condition treatable by the present invention can generally include any autoimmune disease or disorder characterized by activation of the immune system to abnormal levels that lead to the disease or disorder. Examples of autoimmune disease and/or inflammatory conditions that can be treated by the methods of the invention include osteoarthritis, rheumatoid arthritis, septic arthritis, gout, pseudogout, juvenile idiopathic arthritis, Still's disease, Ankylosing spondylitis, lupus erythematosus, sarcoidosis, Henoch-Schönlein purpura, psoriatic arthritis, reactive arthritis, haemochromatosis, hepatitis, Wegener's granulomatosis, Lyme disease, familial mediterranean fever, hyperimmunoglobulinemia D with recurrent fever, TNF receptor associated periodic syndrome, inflammatory bowel disease, and diseases that can mimic arthritis.

In an example of the present invention, a therapeutically effective amount of a pharmaceutical composition comprising bifonazole can be administered to a subject suffering from RA. RA is characterized by a chronic inflammation, loss of bone density, invasion of the articular cartilage by the synovial membrane, and the deformation of the bones in affected joints. One of the pathological hallmarks of RA is the tumor-like expansion of inflamed synovial tissue into the adjacent articular cartilage and bone which causes much of the damage in the diseased joint. The hyperplastic synovium is infiltrated with neutrophils, monocytes, and lymphocytes, immune cells that direct the ongoing local inflammatory response. Synovial invasion, destruction of bone and joint cartilage result from enzymatic degradation of a variety of structural proteins that give the joint its characteristic biomechanical properties. While normal synovial fibroblasts and chondrocytes produce both matrix-degrading proteases (metalloproteases and cysteine proteases) and their inhibitors, in RA the physiological balance is disrupted, resulting in an over production of proteases.

The pharmaceutical composition can be administered to the subject via an intravenous route, for example, in a dosage of about 1 µg to about 1000 mg per day. The composition can be administered over the course of any desired treatment period, such as once daily, twice daily, or more, over any desired number of days, weeks, months, etc. to achieve a therapeutic response in the subject. Administration of the pharmaceutical composition can prevent activity and activation of certain immune cells, such as neutrophils and monocytes as well as prevent cartilage degradation and bone damage.

It should be appreciated that one or more pharmaceutical agents of the present invention can be combined into a single pharmaceutical composition or, alternatively, administered at substantially the same time but as separate pharmaceutical compositions to a subject. Additionally, it will be appreciated that agents other than the pharmaceutical agents provided above can be used as a supplement to, or in conjunction with at least one pharmaceutical agent of the present invention. Non-limiting examples of such other agents can include ant-TNF compounds and IL-I compounds, such as TNF-α inhibitors and IL-I. For example, a therapeutically effective amount of etanercept, a prescription medicine sold under the trademark ENBREL (e.g., a human dose) can be administered to a subject prior to administering a low therapeutic dose of bifonazole. Administering ENBREL prior to bifonazole may at least partially remove or reduce the level and/or activity of TNF-α and thereby increase the therapeutic effect of subsequent bifonazole administration(s).

The following examples are for the purpose of illustration only and are not intended to limit the scope of the claims, which are appended hereto. In the Examples below, bifonazole is referred to as "TC5" and chlorotrianisene is referred to as "TC10" or "NM2026".

EXAMPLE 1

Development of Rheumatoid Arthritis in a Prophylactic Model of Rat Adjuvant Induced Arthritis (AIA)

Lewis rats (Harlan, R #2359) weighing 130-150 grams were received and housed in cages with 3 rats per cage. The animals were placed in quarantine and monitored daily for signs of disease or clinical distress. The rats were marked with ear tags to identify animal number. Following the quarantine period, the animals were moved to a different room for routine maintenance and housing. 75 mg of *Mycobacterium tuberculosis* H37 RA (Difco Cat#231141) was homogenized in 10 ml squalene (Sigma Cat# S-3626) for use as adjuvant. Prior to injection of the adjuvant, the rats were weighed, paw volumes measured, and shaved at the dorsal base of the tail. The rats that received the adjuvant (all rats excluding the non-disease group) were injected with 100 µl of adjuvant intradermally at the base of the tail. The non-disease rats received phosphate buffered saline instead of adjuvant.

Rat weights and paw volumes were measured daily and observed for the development of arthritis. The rats were held for 10 days to allow the development of arthritis. Rats developed arthritis during 10 day to 16 day during which time the paw volume went up with time. For prophylactic evaluation, dosing of the compound started 10 days following adjuvant injection. Prior to injection of the compound, the rats were weighed and the paw volumes measured. At the end of the study, the rats were anesthetized and exsanguinated. The animal limbs were removed and preserved in 10% buffered formalin (Ricca Chemical Co. Cat#3190-1). One limb was evaluated for histology via Hematoxylin and Eosin tissue staining through standard staining methods and the other limb was processed for x-ray radiography and CT scanning Contract services were used to evaluate the histological, radiographic and CT scanning.

EXAMPLE 2

Evaluation of TC5 at 10 mg/Kg/day Dosing in a Male Rat AIA Prophylactic Model

Male rats were subjected to arthritis induction as described in Example 1. In this prophylactic model of AIA, TC5 at 10 mg/kg/day dosing was injected IP in male rats. The paw volumes were measured every day using plethysmometer. The readouts for each rat were plotted against the study day. ENBREL at 30 mg/kg dose was injected only once a week subcutaneously. The animals were dosed for 14 days following which they were euthanized for other readouts.

Figure 2:
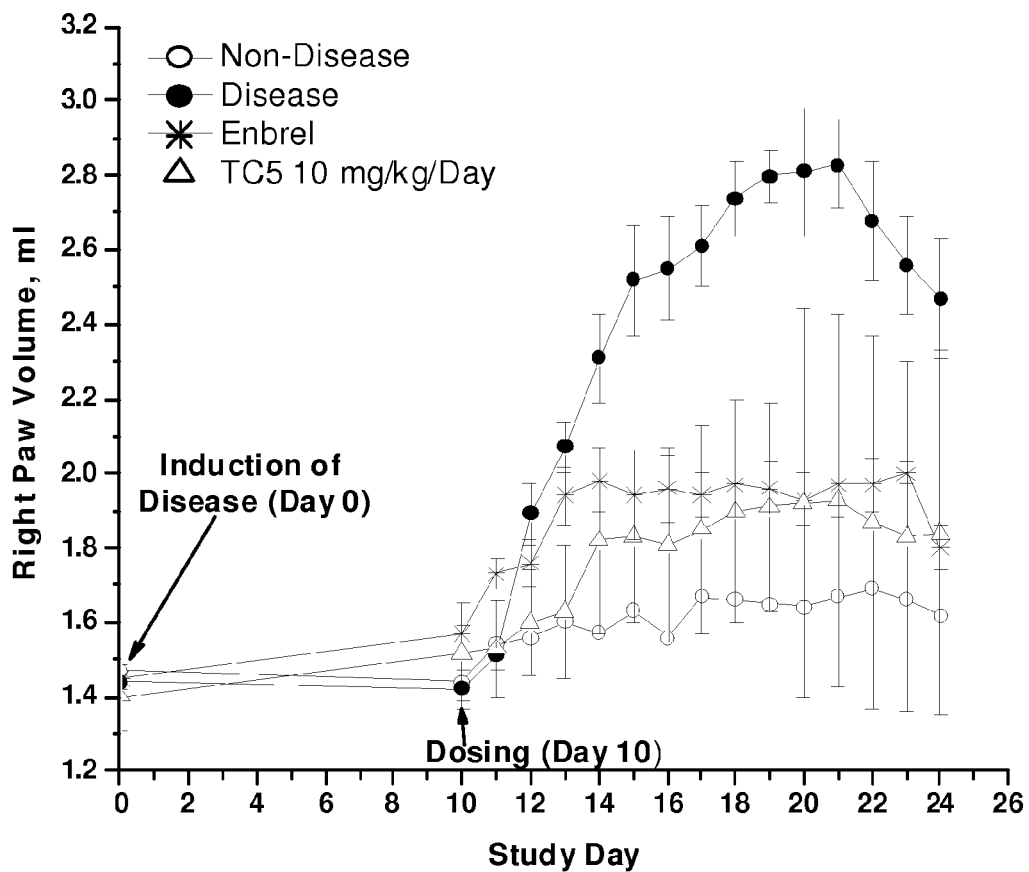
FIG. 2 is a graph showing the effect of TC5 on right paw inflammation in a prophylactic model of rat AIA. TC5 was administered intraperitoneally at 10 mg/kg/day. The administration was given prophylactically at day 10 to demonstrate prevention of arthritis in rats. Development of arthritis usually takes 14 days to progress. TC5 was administered at day 10 and inhibition of arthritis was measured on right paw inflammation.
Figure 3:
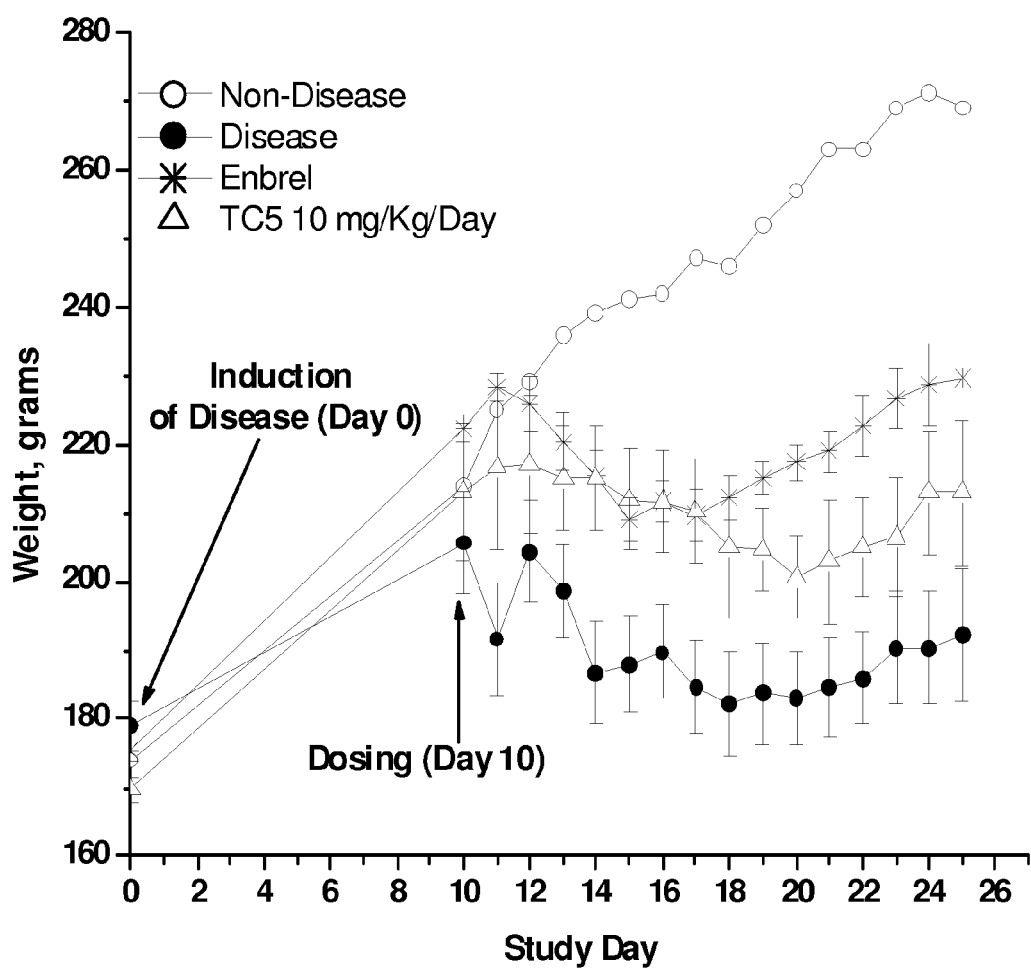
FIG. 3 is a graph showing the effect of TC5 on rat weight in a prophylactic model of rat AIA (IP dosing). The rats described in FIGS. 1-2 were measured for drug effects on weight. Diseased animals tend not to gain weight, as demonstrated by FIG. 3. This is compared against the non-disease animals, which do gain weight. Treatment with TC5 does not adversely affect rat weight and gives results comparable to the positive control ENBREL.

As shown in FIGS. 1-2, TC 5 reduced paw inflammation to control levels similar to those observed for ENBREL. ENBREL was used as a positive control Animals were also weighed at each time points. Weight loss was found to be near negligible compared to control ENBREL group as shown in FIG. 3. The large error bars reflect smaller group size.

Figure 4:
FIG. 4 is a series of radiographs showing the effect of TC5 on joint damage in a prophylactic model of rat AIA (IP dosing). At the termination of the study, the rat limbs were harvested and evaluated for joint damage. The limbs were evaluated for joint damage using x-ray radiography. The radiographs demonstrate that TC5 is able to prevent significant joint damage compared to the disease control. This prevention of joint damage is similar to the effects observed by the positive control ENBREL.
Figure 5:
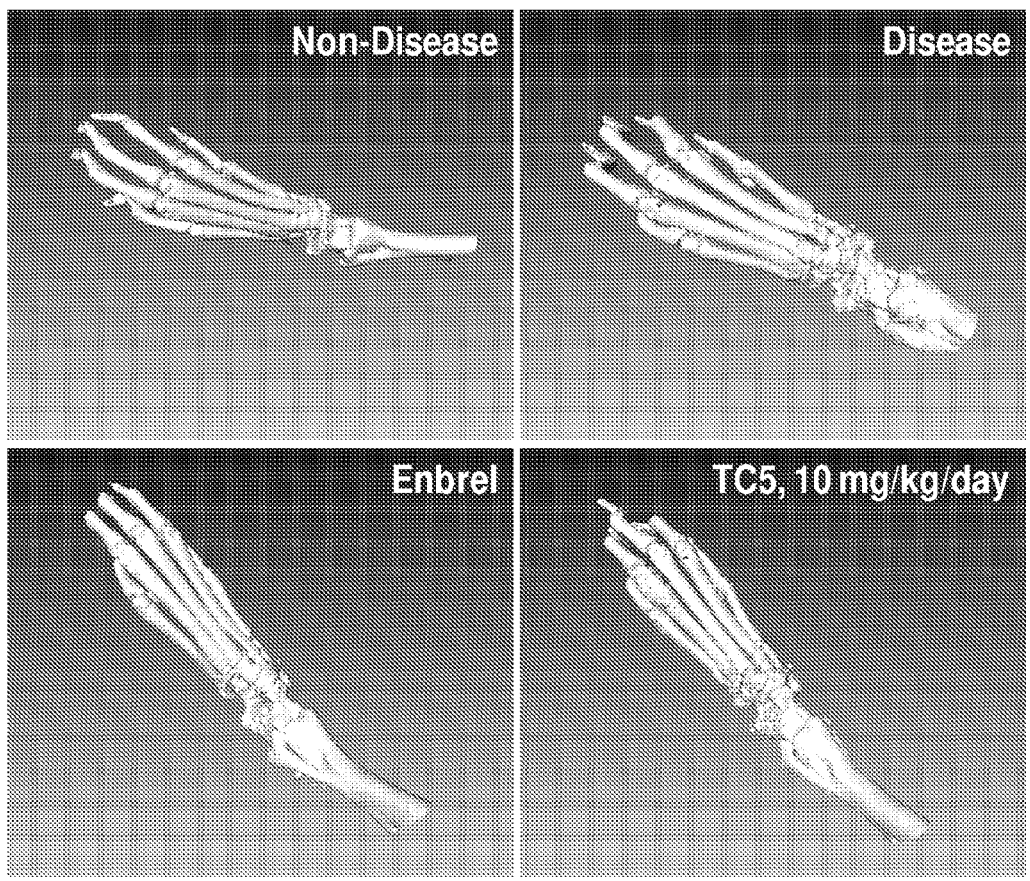
FIG. 5 is a series of CT scans showing the effect of TC5 on joint damage in a prophylactic model of rat AIA (IP dosing). The same limbs described in FIG. 4 were evaluated for joint damage using CT scanning. The benefit of CT scanning is that it provides clearer imaging of joint structure than the radiograph. As observed in FIG. 5, there is significant reduction in bone damage in treated animals compared to diseased animals.
Figure 6:
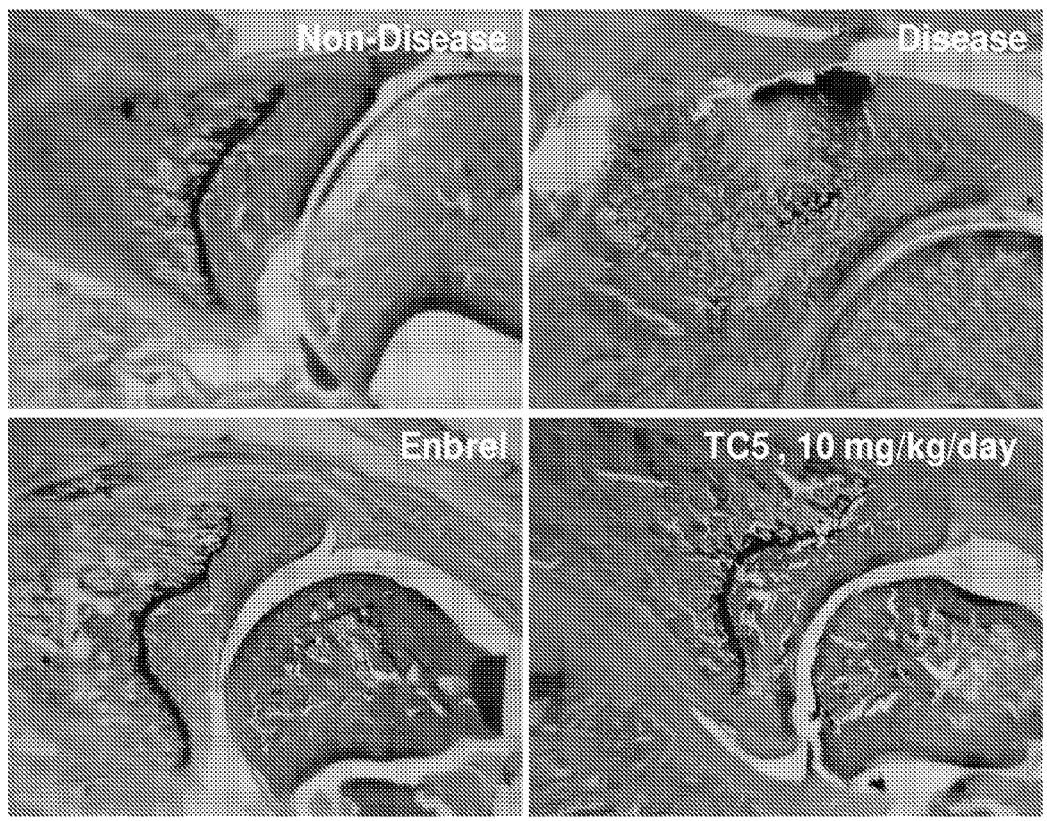
FIG. 6 is a series of histological images showing histological assessment of the effect of TC5 on joint histology in a prophylactic model of rat AIA (IP dosing). At the termination of the rat study, the limbs were harvested and one limb was evaluated for histology using standard H&E staining. As demonstrated in FIG. 6, TC5 demonstrates significant preservation of the synovium membrane (white space), significant preservation of the cartilage (space between the 2 blue lines), and minor bone proliferation. This is a significant difference compared to the diseased animal, where the cartilage and synovium are significantly damaged.

Radiographs shown in FIG. 4 demonstrate that TC5 was effective is preserving the joint damage. FIG. 5 shows corresponding CT scan. These CAT scan images match well with the radiographs. Shown in FIG. 6 are histological images of the joint. As observed in the disease control, there is significant bone proliferation, accompanied with inflammation, total dissolution of the cartilage, and collapse of the synovial space. In the TC5 treated rats, the joint closely resembles the non-disease control animals. There is minimal inflammation, reduced bone proliferation, preservation of the cartilage, and preservation of the synovial membrane. These are important considerations for the treatment of rheumatoid arthritis. As shown TC5 prevents joint damage similar to those from ENBREL treated group. Disease group shows massive inflammation and joint damage.

EXAMPLE 3

Evaluation of TC5 at 2.5 mg/Kg/day and 500 ug/Kg/Day Dosing in a Male Rat AIA Prophylactic Model Male rats were subjected to arthritis induction as described in Example 1. In this prophylactic model of AIA, TC5 at 2.5 mg/kg/day dosing or 500 µg/kg/day was injected IP in male rats. The paw volumes were measured every day using plethysmometer. The readouts for each rat were plotted against the study day. ENBREL at 30 mg/kg dose was injected only once a week subcutaneously as a positive control. The animals were dosed for 14 days following which they were euthanized for other readouts.

Figure 7:
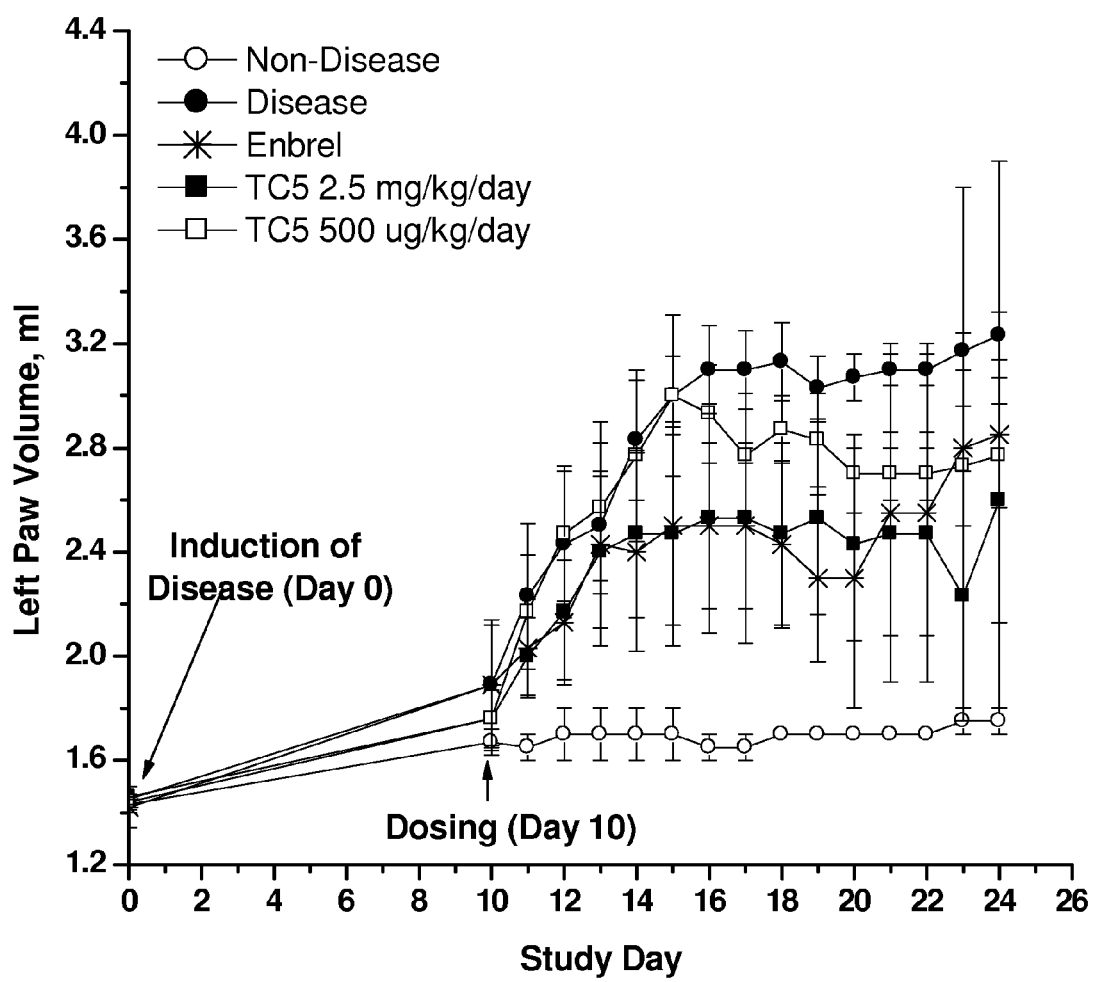
FIG. 7 is a graph showing the effect of 2.5 mg and 500 µg per kg dosing of TC5 on paw inflammation in a prophylactic model of rat AIA (left paw, IP dosing). TC5 was administered intraperitoneally at different doses in a rat model of adjuvant-induced arthritis to evaluate dose effects of TC5. The administration was given prophylactically at day 10 to demonstrate prevention of polyarthritis in rats. These results indicate that TC5 can prevent development and progression of rat adjuvant induced arthritis dose dependently with maximum effect observed at 500 µg/rat/day dosing. This dose demonstrates comparable results to ENBREL.
Figure 8:
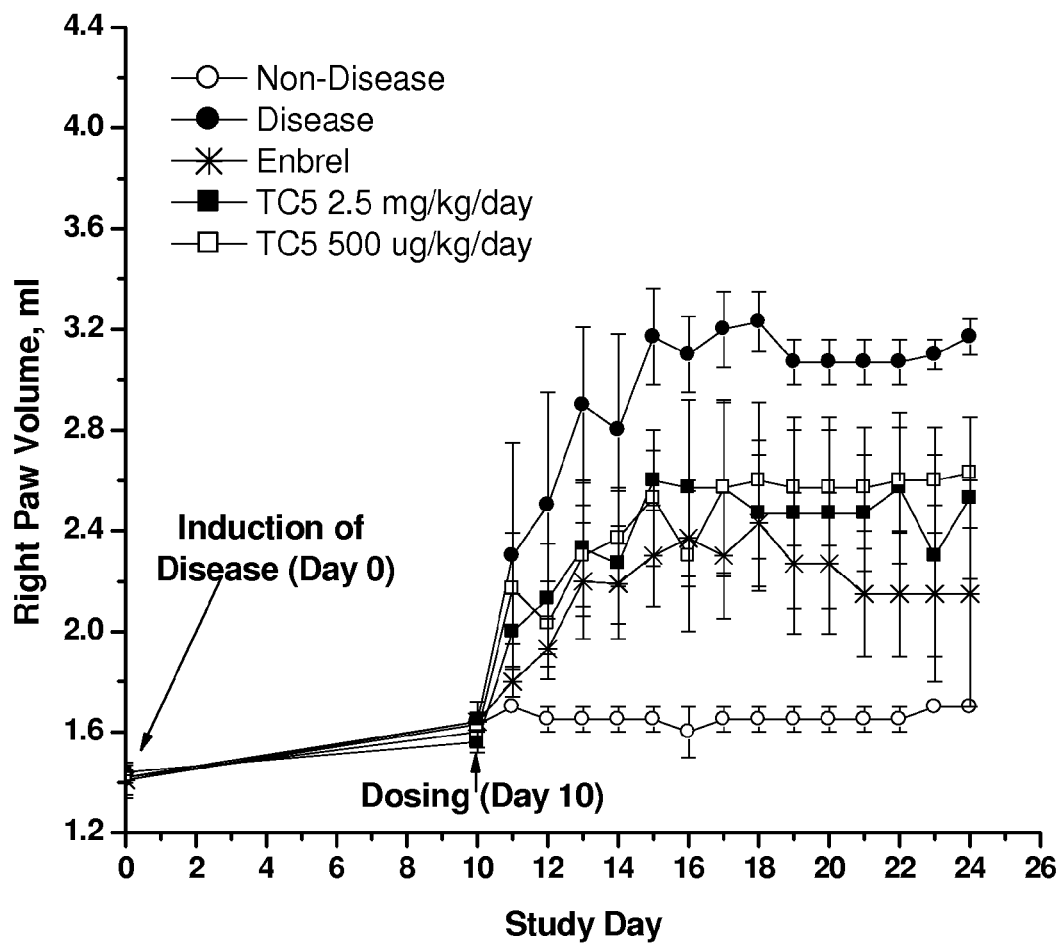
FIG. 8 is a graph showing the effect of TC5 at 2.5 mg and 500 µg per kg on paw inflammation in a prophylactic model of rat AIA (right paw, IP dosing). The same rats described in FIG. 7 were evaluated for right paw inflammation. The results are similar with maximum inhibition observed at the 500 µg/kg/day.
Figure 9:
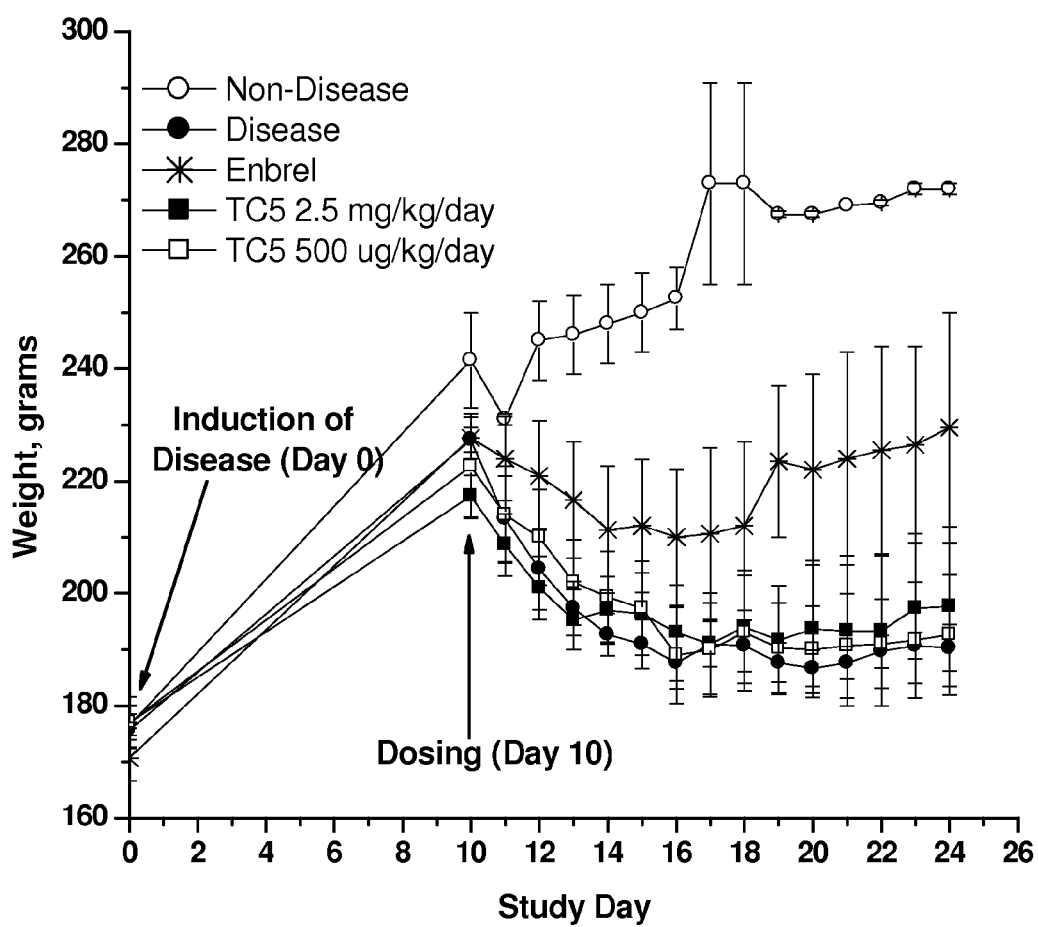
FIG. 9 is a graph showing the effect of TC5 at 2.5 mg and 500 µg per kg on rat weight in a prophylactic model of rat AIA (IP dosing). The rats described in FIGS. 7-8 were measured for drug effects on weight. Diseased animals tend not to gain weight as demonstrated by the figure. This is compared against the non-disease animals, which do gain weight. Treatment with TC5 does not adversely affect rat weight and gives results comparable to diseased animals. This indicates that TC5 does not adversely affect the rat weight.

As shown in FIGS. 7-8, TC 5 at 2.5 mg/kg demonstrated maximal effect similar to ENBREL. A lower dose of 500 µg/kg/day also reduced paw inflammation. ENBREL was used as a positive control. Animals were weighed at each time point. Weight loss was found to be near negligible compared to disease group as shown in FIG. 9. The large error bars reflect smaller group size.

Figure 10:
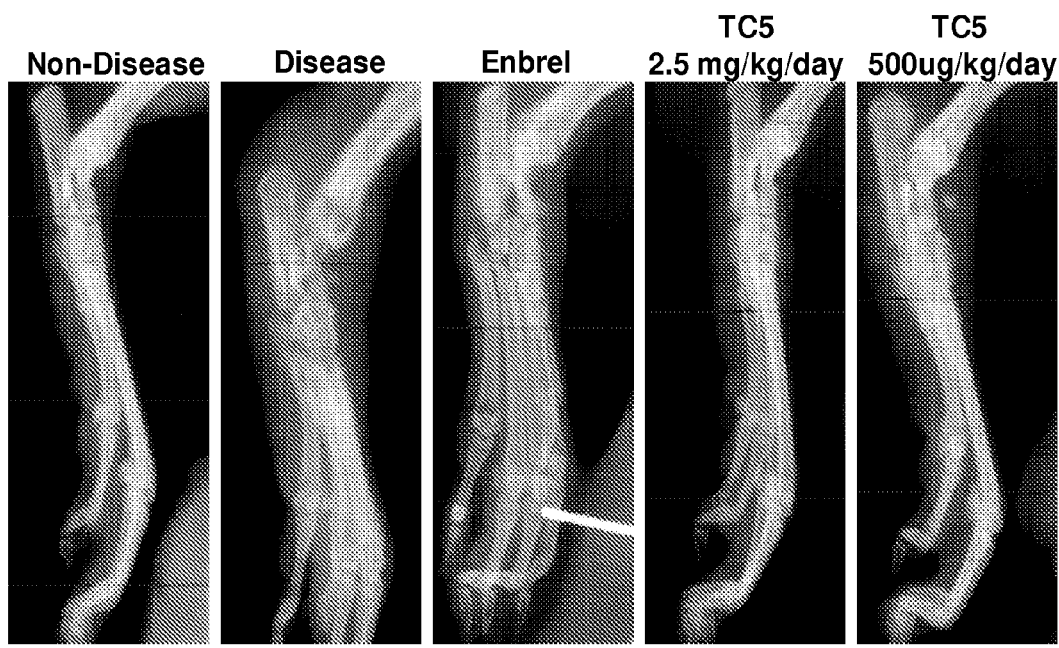
FIG. 10 is a series of radiographs showing the effect of TC5 dosing of 2.5 and 500 µg/kg on joint damage in a prophylactic model of rat AIA (IP dosing). At the termination of the study, the rat limbs were harvested and evaluated for joint damage. The limbs were evaluated for joint damage using x-ray radiography. The radiographs demonstrate that TC5 is able to prevent significant joint damage compared to the disease control in a dose dependent manner. Maximal prevention of joint damage is observed at the highest dose of 500 µg/kg.

Radiographs shown in FIG. 10 demonstrate that TC5 was effective is preserving the joint damage at both concentrations. Thus, TC5 prevents joint damage similar to those from ENBREL treated group. Disease group shows massive inflammation and joint damage.

EXAMPLE 4

Evaluation of Oral Dosing of TC5 at 5, 2.5, and 0.5 mg/Kg/day Dosing in a Male Rat AIA Prophylactic Model Male rats were subjected to arthritis induction as described in Example 1. In this prophylactic model of AIA, TC5 at 5, 2.5, and 0.5 mg/kg/day dosing was given by oral gavage in male rats. The paw volumes were measured every day using plethysmometer. The readouts for each rat were plotted against the study day. ENBREL at 30 mg/kg dose was injected only once a week subcutaneously as a positive control. The animals were dosed for 14 days following which they were euthanized for other readouts.

Figure 11:
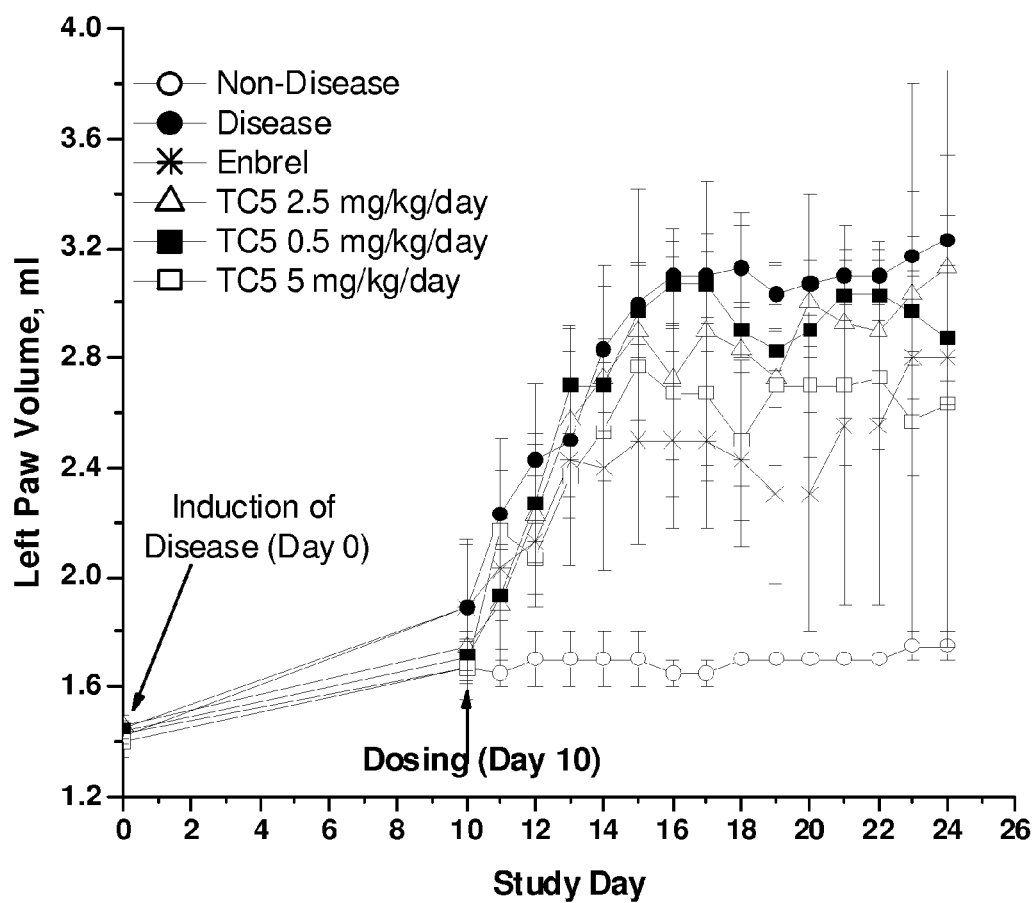
FIG. 11 is a graph showing the effect of oral dosing of TC5 on paw inflammation in a prophylactic model of rat AIA (left paw, oral dosing). TC5 was administered orally at different doses in a rat model of adjuvant-induced arthritis to evaluate dose effects of TC5. The administration was given prophylactically at day 10 to demonstrate prevention of polyarthritis in rats. These results indicate that TC5 can prevent development and progression of rat adjuvant induced arthritis dose dependently with maximum effect observed at 500 µg/kg/day. These results are not as effective as the IP dosing due to the oral administration. This decrease in potency is due to the limited bioavailability of the compound via oral administration.
Figure 12:
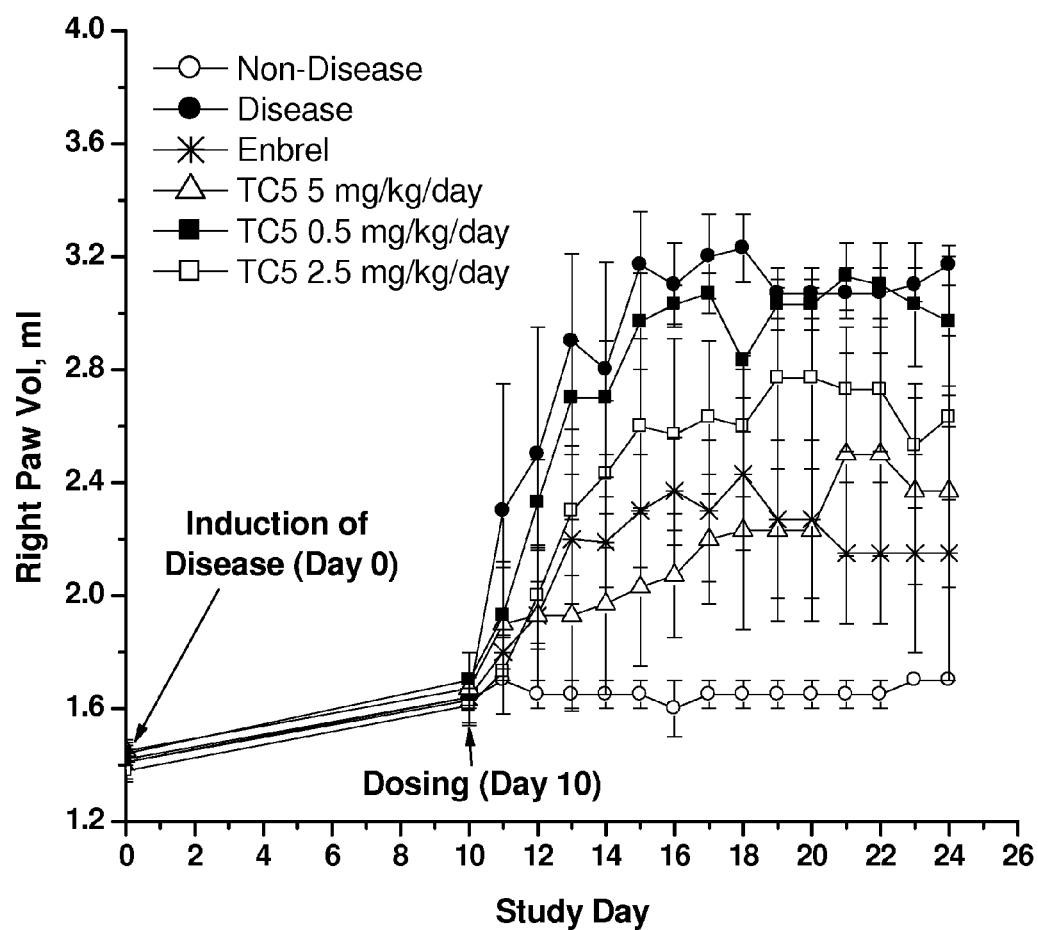
FIG. 12 is a graph showing the effect of TC5 on paw inflammation in a prophylactic model of rat AIA (right paw, oral dosing). The same rats described in FIG. 11 were evaluated for right paw inflammation. The results are similar to left paw inflammation.
Figure 13:
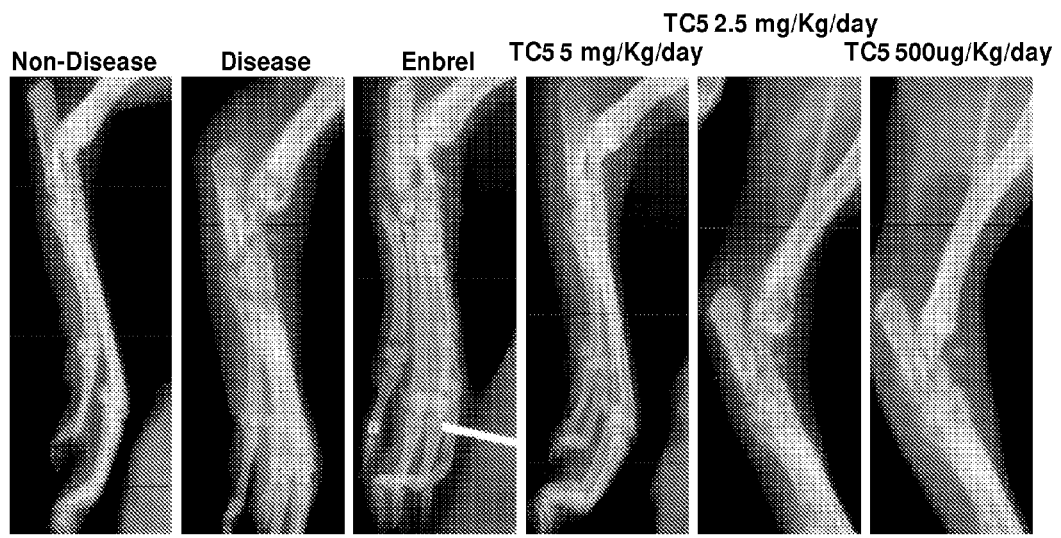
FIG. 13 is a series of radiographs showing the effect of TC5 on paw inflammation in a prophylactic model of rat AIA (right paw, oral dosing). The same rats described in FIG. 11 were evaluated for right paw inflammation. The results are similar to left paw inflammation.
Figure 14:
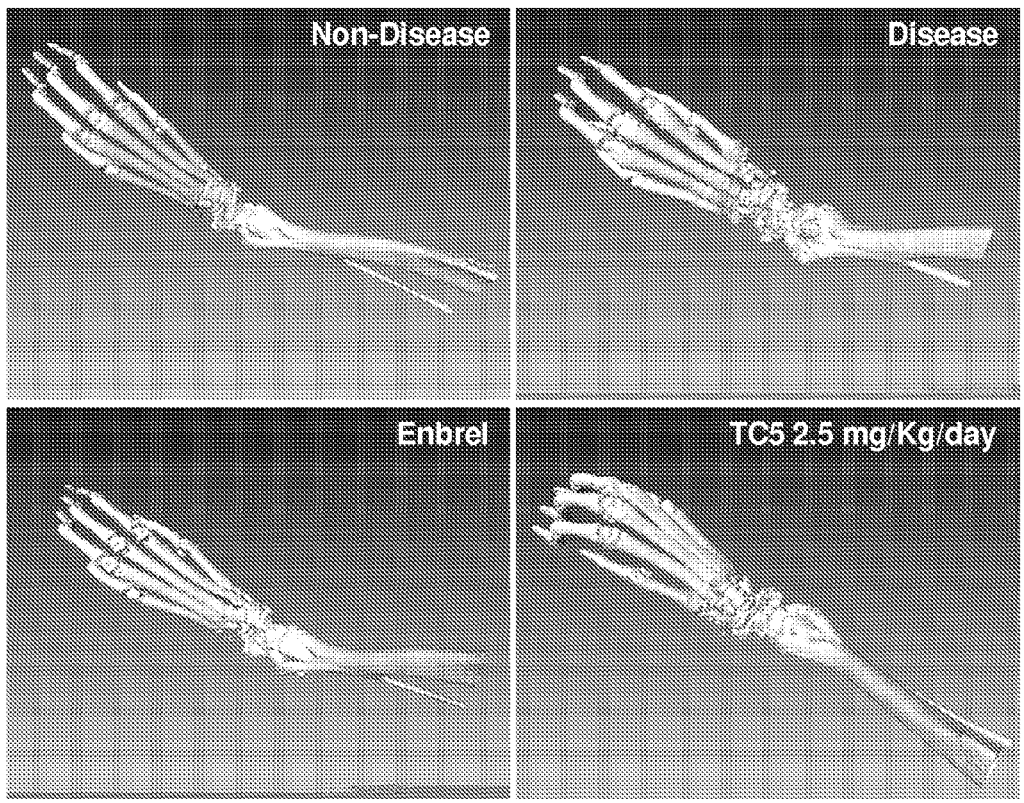
FIG. 14 is a series of CT scans showing the effect of TC5 on joint damage in a prophylactic model of rat AIA (IP dosing). The same limbs described in FIG. 13 were evaluated for joint damage using CT scanning. The benefit of CT scanning is that it provides clearer imaging of joint structure than the radiograph. As observed in the figure there is significant reduction in bone damage in treated animals compared to diseased animals. CT scans were done for only one group. Scanning was done on the 500 µg/Kg oral group to demonstrate that even the medium dose is still able to prevent significant bone destruction compared to the diseased control.

As shown in FIGS. 11-12, TC 5 effect on paw volume was dose dependent with the highest dose demonstrated maximal effect. Radiographs shown in FIG. 13 demonstrate that TC5 was effective in preserving the joint damage at all three concentrations tested. CT scan results are shown in FIG. 14. Thus, TC5 prevents joint damage similar to those from ENBREL treated group. Disease group shows massive inflammation and joint damage.

EXAMPLE 5

Figure 15:
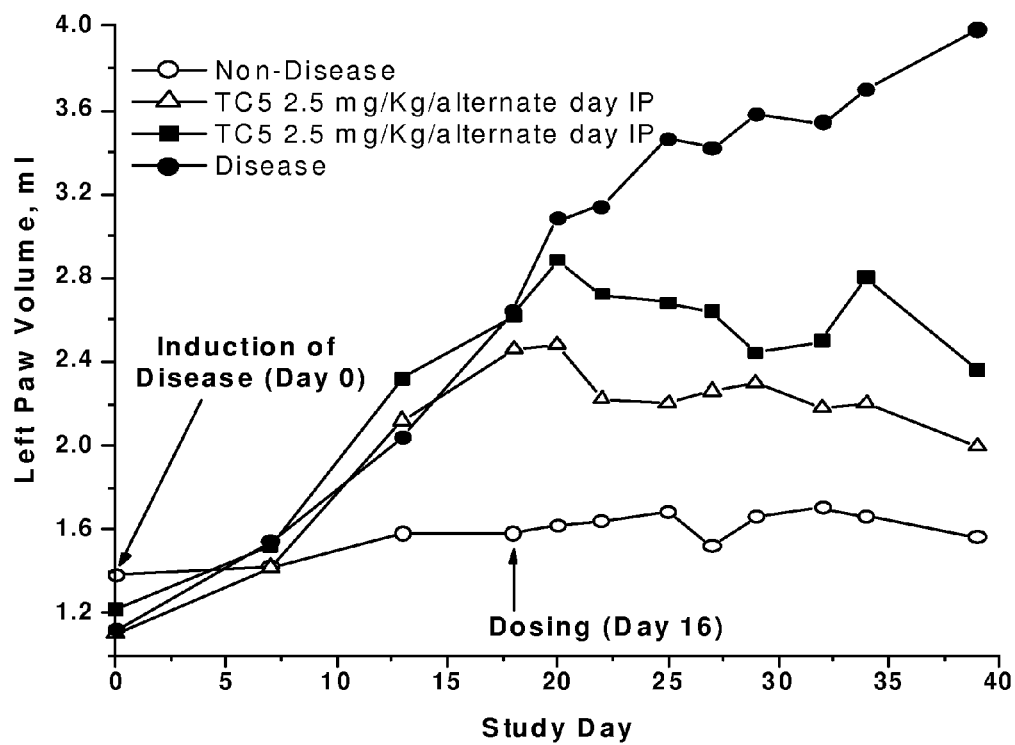
FIG. 15 is a graph showing the effect of TC5 on paw inflammation in a therapeutic model of rat AIA (left paw, IP dosing). A similar rat AIA study was conducted with limited number of animals. The difference between the prophylactic and established disease models is that dosing starts at day 16 once arthritis has developed as opposed to day 10. This model measures the effect of a drug to prevent progression of developed arthritic condition. As demonstrated, TC5 is able to halt the progression of the disease.
Figure 16:
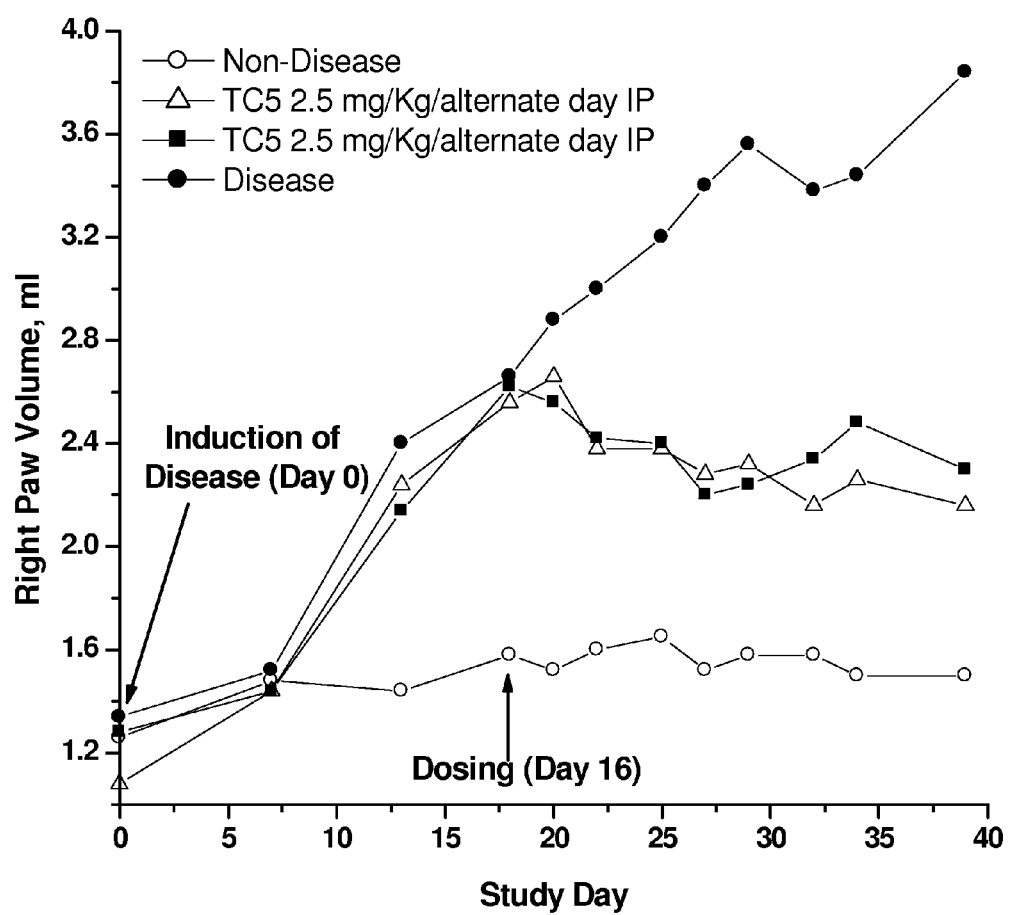
FIG. 16 is a graph showing the effect of TC5 on paw inflammation in an established model of rat AIA (right paw, IP dosing). The study described in FIG. 15 is the same FIG. 16 with the only difference being that right paw inflammation was evaluated. Similar results on TC5 prevention of arthritic progression are observed.
Figure 17:
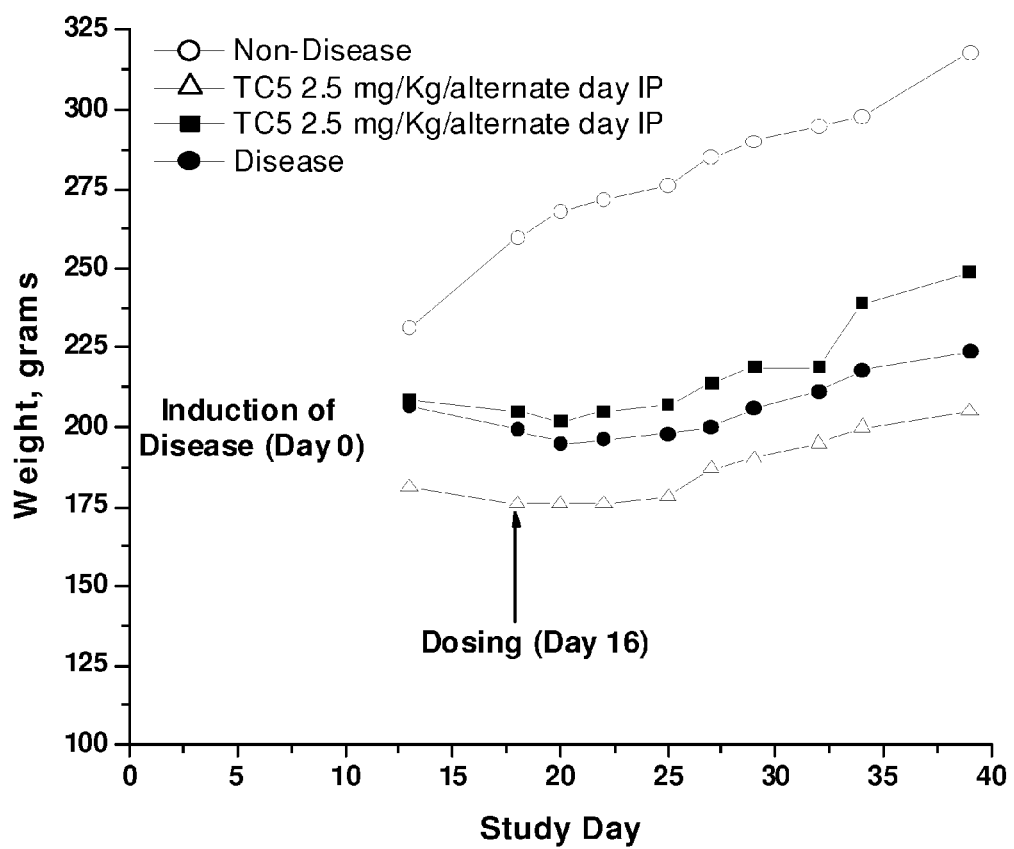
FIG. 17 is a graph showing the effect of TC5 on rat weight in an established model of rat AIA (IP dosing). The rat weights were evaluated in this model of the disease. Treatment of TC5 demonstrates no adverse effects on rat weight.
Figure 18:
FIG. 18 is a series of radiographs showing the effect of TC5 on right ankle damage in an established model of rat AIA (IP dosing). At the termination of the study, the limbs were harvested and evaluated for joint damage using radiographic analysis. The radiographs demonstrate significant bone destruction in the diseased control. TC5 treatment is able to limit the extent of damage. This indicates that TC5 can be used to halt the progression of the disease.

Evaluation of IP Dosing of TC5 at 2.5 mg/Kg/Alternate Day Dosing in a Male Rat AIA Established Disease Model Male rats were subjected to arthritis induction as described in Example 1. Rats were allowed to develop the disease past day 10 into day 16 during which time animals were half way into the disease. Dosing started at day 16. The animals were dosed 2.5 mg/kg every other day until day 40. The study was extended for an additional 16 days to allow maximal response to occur. The paw volumes were measured every other day before the dosing using plethysmometer. The readouts for each rat were plotted against the study day. ENBREL at 30 mg/kg dose was injected only once a week subcutaneously as a positive control. The animals were given 13 doses up until day 40. Dosing started at day 16 and continued until day 40. As shown in FIGS. 15-16, TC 5 halted the progression of the disease. Radiographs shown in FIG. 17 demonstrate that TC5 was effective in preserving the joint damage compared to disease controls.

EXAMPLE 6

Evaluation of TC5 in a Mouse Collagen-Induced Arthritis (CIA) Model

Male DBA/J1 mice (7-9 weeks old from Jackson Labs, Bar Harbor, Me., USA) were used. The CIA study using mice of same age, strain and source was performed at Boulder Bio-PATH Inc as described below. Male DBA/J1 mice were shaved at the base of the tail and injected with 0.1 ml emulsion consisting of a 1 to 1 (1 mg/1 mg) mixture of type II chicken collagen with *Mycobacterium butyricum* (Difco) as an adjuvant. Three weeks later, the mice were boosted with another 0.1 ml injection of emulsion at the base of the tail to induce disease. Dosing started at day 18 while the last boost to induce the disease was at day 21. The mice were scored in a blinded manner twice weekly for 3 weeks for signs of arthritis in each paw according to the following scale: clinical signs were evaluated using the following scale: 0=normal; 1=one joint affected or mild diffuse erythema and swelling; 2=two joints affected or mild diffuse erythema and swelling; 3=three joints affected or mild diffuse erythema and swelling; 4=four joint affected or marked diffuse erythema and swelling; and 5=severe erythema and severe swelling. Upon study completion (day 28), mice were killed with $CO_2$.

Figure 19:
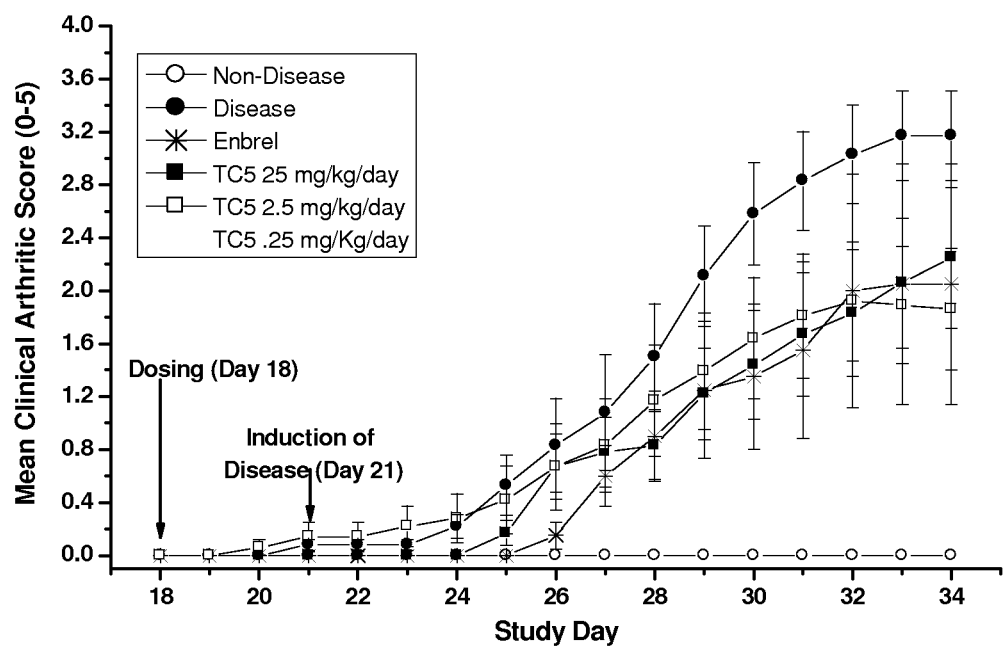
FIG. 19 is a graph showing the effect of TC5 on paw inflammation in prophylactic model of mouse CIA (IP dosing). TC5 was evaluated in a mouse model of collagen-induced arthritis (CIA). This model is another standard model of arthritis for drug evaluation. The effect of arthritic development is measured based on clinical scoring of the paws. TC5 was administered at different doses in this study and were found to have significant prevention of arthritis with inhibition comparable to ENBREL.

As shown in FIG. 19, there were 9 animals per group with 6 in control disease and non-disease groups. Both 2.5 and 0.25 mg/kg doses inhibited clinical signs of the disease comparable to ENBREL treated groups. These studies suggest that TC 5 may be a viable candidate for the treatment of arthritis. Additional studies are underway to fully characterize the effect of Tc5 in mouse CIA.

EXAMPLE 7

Evaluation of TC10 at 10 mg/Kg/day Dosing in a Male Rat AIA Prophylactic Model

Male rats were subjected to arthritis induction as described in Example 1. In this prophylactic model of AIA, TC10 at 10 mg/kg/day dosing was injected IP in male rats. The paw volumes were measured every day using plethysmometer. The readouts for each rat were plotted against the study day. ENBREL at 30 mg/kg dose was injected only once a week subcutaneously. The animals were dosed for 14 days following which they were euthanized for other readouts.

Figure 20:
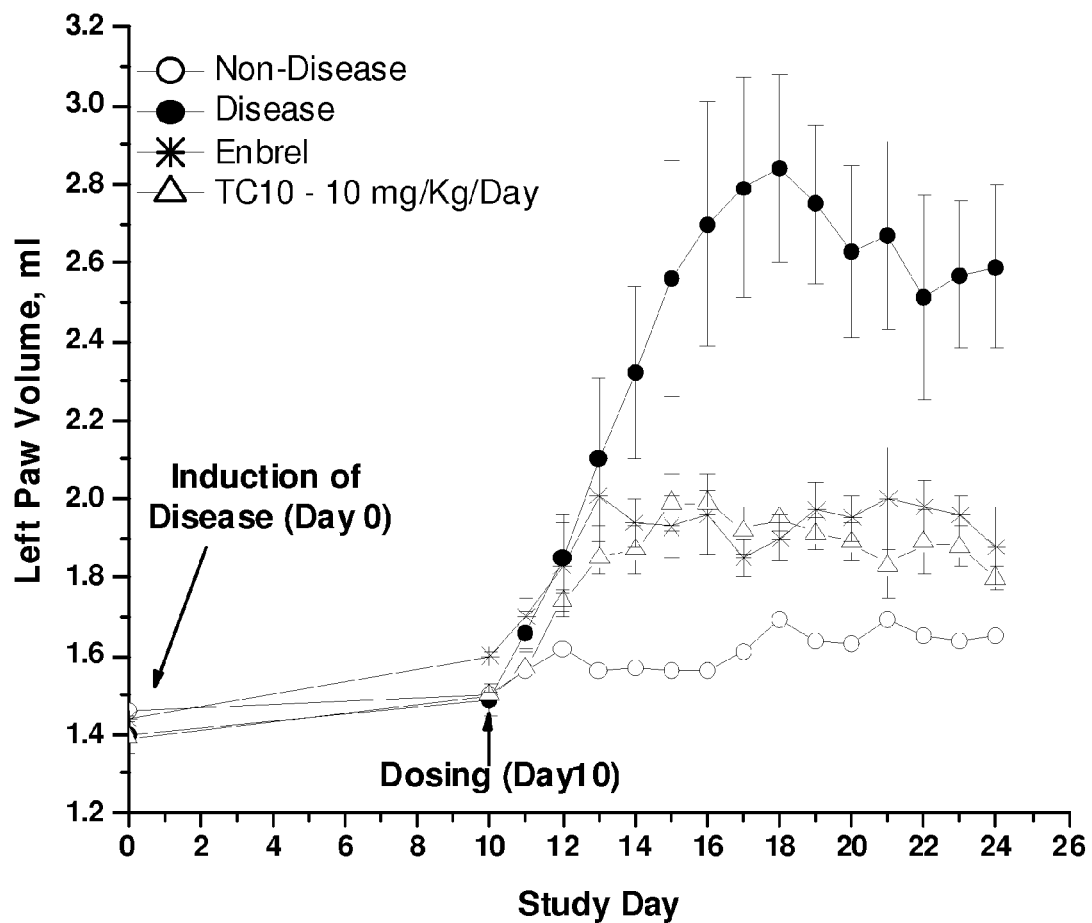
FIG. 20 is a graph showing the effect of chlorotrianisene (hereinafter, "TC10") on paw inflammation in a prophylactic model of rat AIA (left Paw, IP dosing). TC10 was administered intraperitoneally at 10 mg/kg/day in a rat model of adjuvant-induced arthritis. The administration was given prophylactically at day 10 to demonstrate prevention of arthritis in rats. Development of arthritis usually takes 14 days to progress. TC10 was administered at day 10 and inhibition of arthritis was measured on left paw inflammation. These results indicate that TC10 can prevent development and progression of rat adjuvant induced arthritis comparable to the effects of ENBREL, a current standard of care for the treatment of rheumatoid arthritis.
Figure 21:
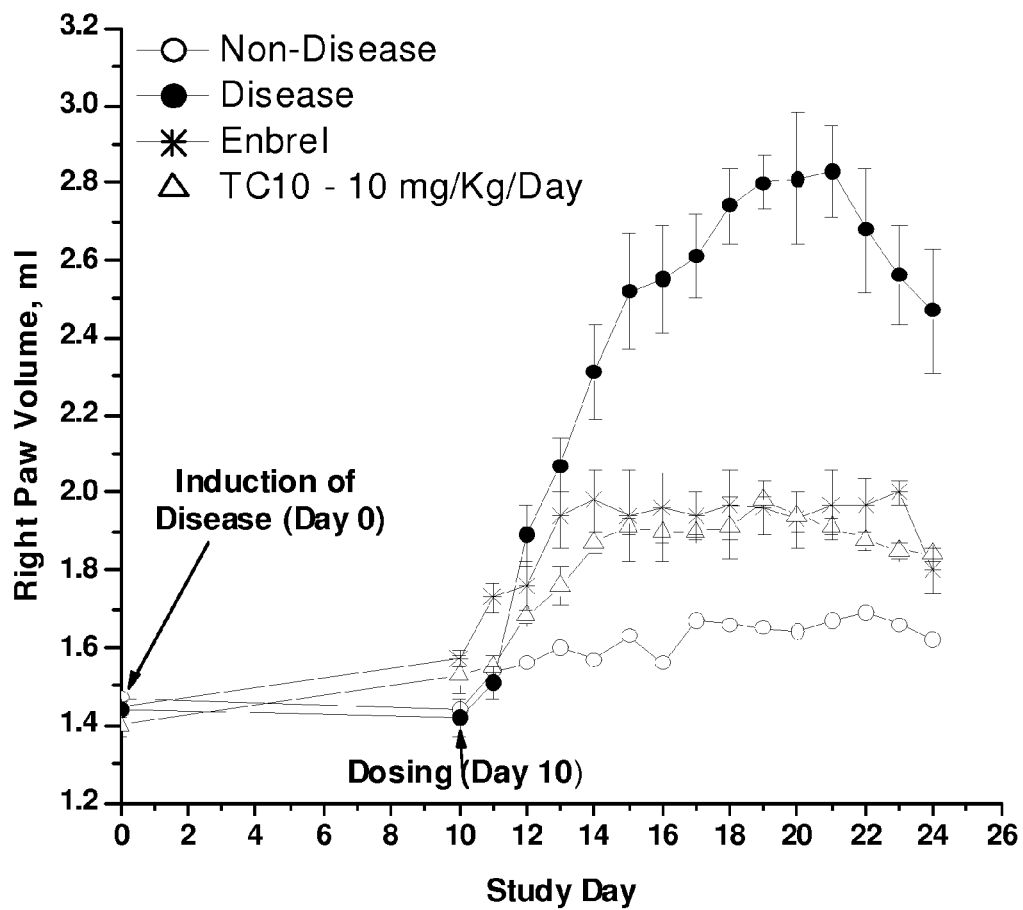
FIG. 21 is a graph showing the effect of TC10 on paw inflammation in a prophylactic model of rat AIA (right paw, IP dosing). TC10 was administered intraperitoneally at 10 mg/kg/day in a rat model of adjuvant-induced arthritis similar to as described for FIG. 20. The same rats were evaluated for right paw inflammation. TC10 was able to inhibit paw inflammation similar to the effects of ENBREL.
Figure 22:
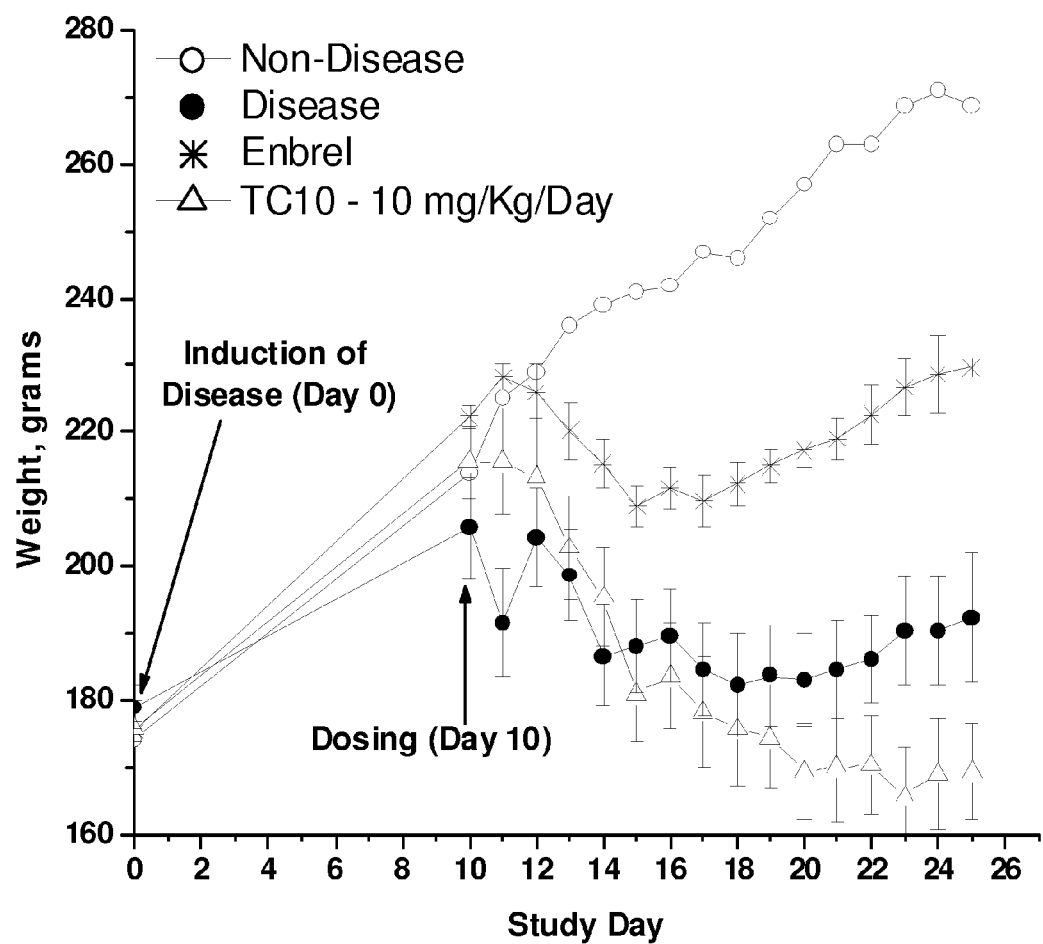
FIG. 22 is a graph showing the effect of TC10 on rat weight in a prophylactic model of rat AIA (IP dosing). The rats described in FIGS. 1-2 were measured for drug effects on weight. Diseased animals tend not to gain weight as demonstrated by FIG. 22. This is compared against the non-disease animals, which do gain weight. Treatment with TC10 does not adversely affect rat weight compared to the weight at day 0.

As shown in FIGS. 20-21, TC 10 reduced paw inflammation to control levels similar to those observed for ENBREL. ENBREL was used as a positive control. Animals were also weighed at each time points. Weight loss was found to be near negligible compared to control ENBREL group as shown in FIG. 22. The large error bars reflect smaller group size.

Figure 23:
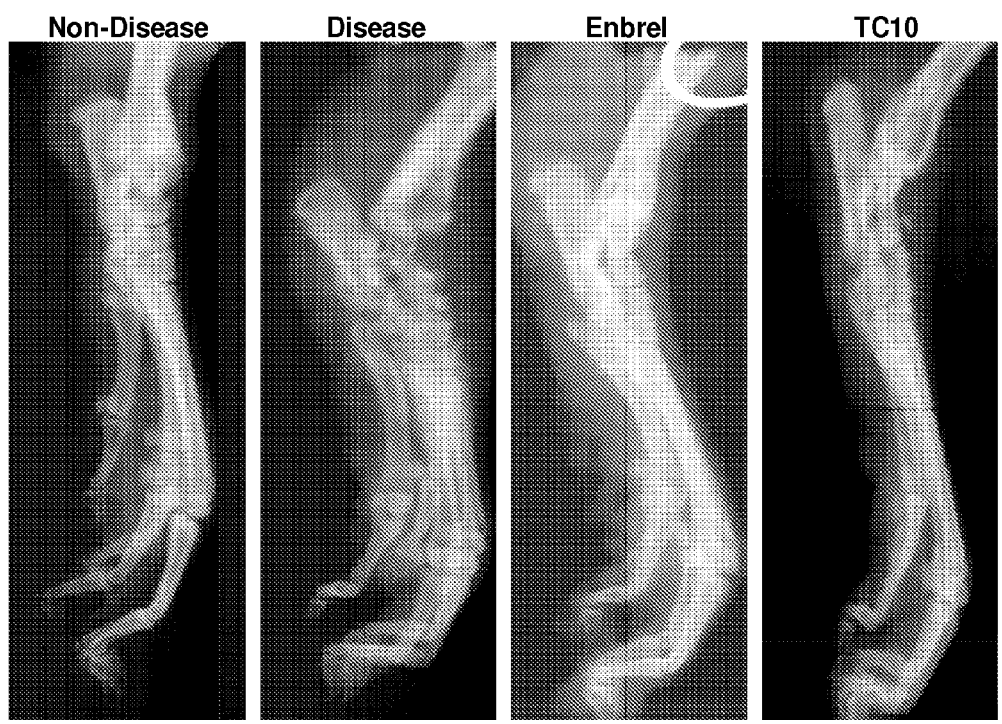
FIG. 23 is a series of radiographs showing the effect of TC10 on joint damage in a prophylactic model of rat AIA (IP dosing). At the termination of the study, the rat limbs were harvested and evaluated for joint damage. The limbs were evaluated for joint damage using x-ray radiography. The radiographs demonstrate that TC10 is able to prevent significant joint damage compared to the disease control. This prevention of joint damage is similar to the effects observed by the positive control ENBREL.
Figure 24:
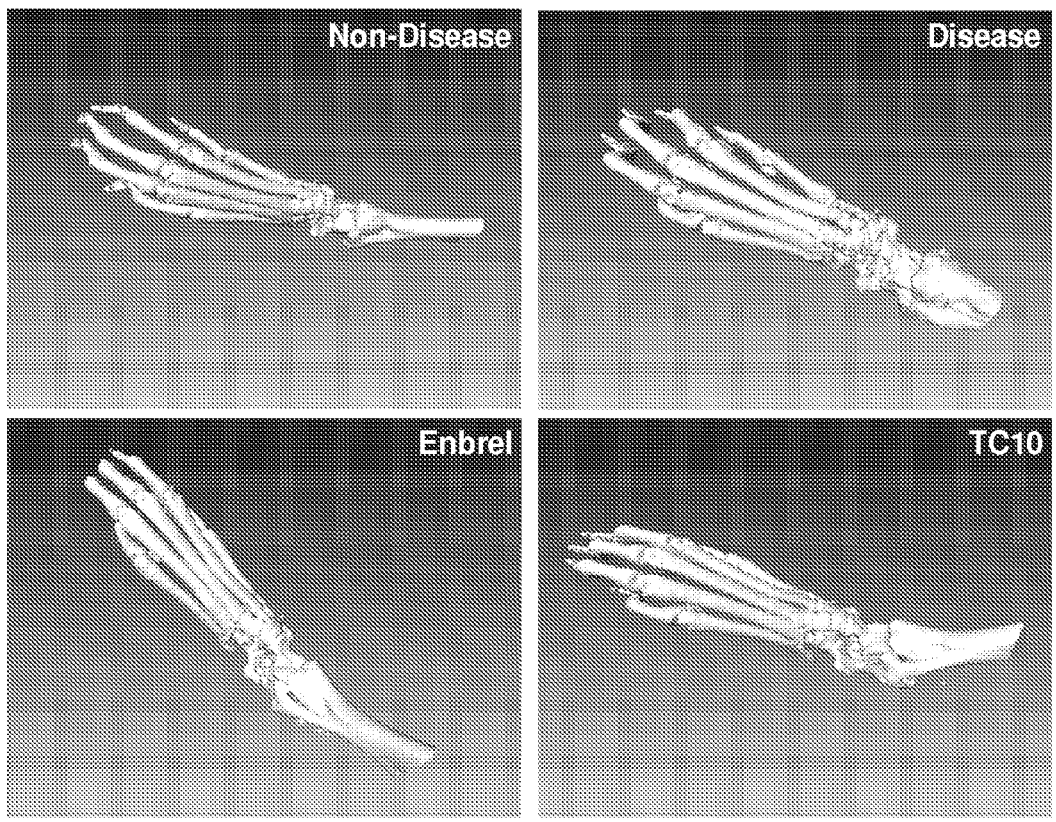
FIG. 24 is a series of CT scans showing the effect of TC10 on joint damage in a prophylactic model of rat AIA (IP dosing). The same limbs described in FIG. 20 were evaluated for joint damage using CT scanning. The benefit of CT scanning is that it provides clearer imaging of joint structure than the radiograph. As observed in FIG. 24, there is significant reduction in bone damage in treated animals compared to diseased animals.
Figure 25:
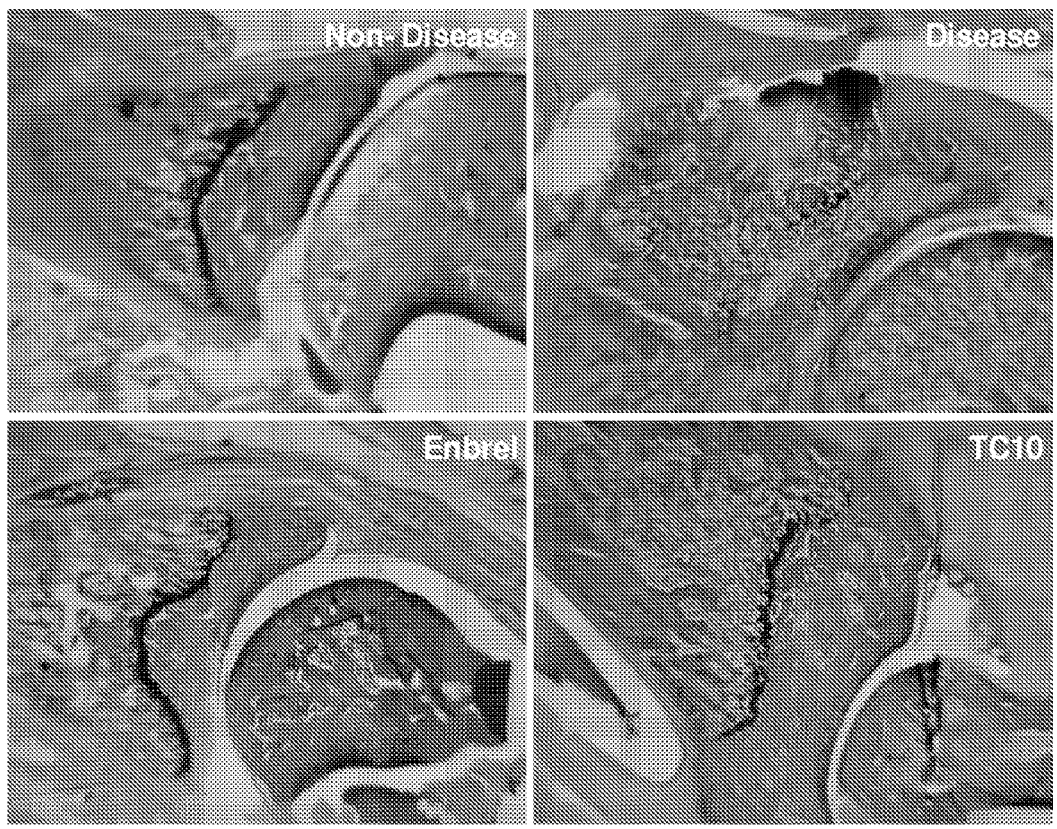
FIG. 25 is a series of histological images showing the effect of TC10 on joint histology in a prophylactic model of rat AIA (IP dosing). At the termination of the rat study, the limbs were harvested and one limb was evaluated for histology using standard H&E staining. As demonstrated in FIG. 25, TC10 demonstrates significant preservation of the synovium membrane (white space), significant preservation of the cartilage (space between the 2 blue lines), and minor bone proliferation. This is a significant difference compared to the diseased animal, where the cartilage and synovium are significantly damaged.

Radiographs shown in FIG. 23 demonstrate that TC10 was effective is preserving the joint damage. FIG. 24 shows corresponding CT scan. These CAT scan images match well with the radiographs. Shown in FIG. 25 are histological images of the joint. As observed in the disease control, there is significant bone proliferation, accompanied with inflammation, total dissolution of the cartilage, and collapse of the synovial space. In the TC10 treated rats, the joint closely resembles the non-disease control animals. There is minimal inflammation, reduced bone proliferation, preservation of the cartilage, and preservation of the synovial membrane. These are important considerations for the treatment of rheumatoid arthritis. As shown TC10 prevents joint damage similar to those from ENBREL treated group. Disease group shows massive inflammation and joint damage.

EXAMPLE 8

Evaluation of TC5 at 2.5 mg/Kg/day and 500 ug/Kg/Day Dosing in a Male Rat AIA Prophylactic Model Male rats were subjected to arthritis induction as described in Example 1. In this prophylactic model of AIA, TC10 at 2.5 mg/Kg/Day dosing or 500 µg/kg/day was injected IP in male rats. The paw volumes were measured every day using plethysmometer. The readouts for each rat were plotted against the study day. ENBREL at 30 mg/kg dose was injected only once a week subcutaneously as a positive control. The animals were dosed for 14 days following which they were euthanized for other readouts.

Figure 26:
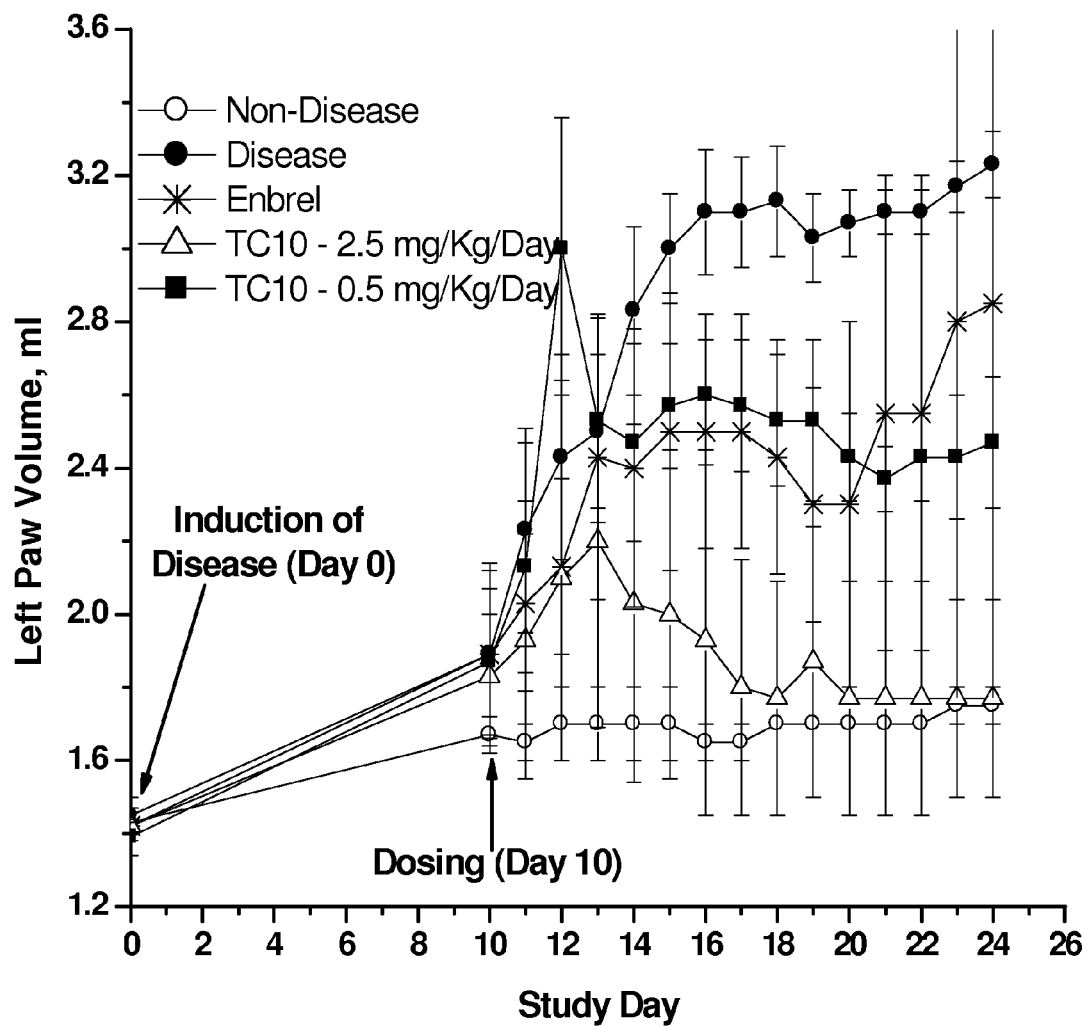
FIG. 26 is a graph showing the effect of TC10 on paw inflammation in a prophylactic model of rat AIA (left paw, IP dosing). TC10 was administered intraperitoneally at 2.5 and 0.5 mg/kg/day in a rat model of adjuvant-induced arthritis to evaluate dose effects of TC10. The administration was given prophylactically at day 10 to demonstrate prevention of arthritis in rats. These results indicate that TC10 can prevent development and progression of rat adjuvant induced arthritis dose dependently with maximum effect observed at 2.5 dose. This dose demonstrates near complete prevention of arthritis bringing paw inflammation near the non-disease control. The lower dose of 500 μg gives results comparable results to ENBREL. These results demonstrate the potency of TC10 on paw inflammation.
Figure 27:
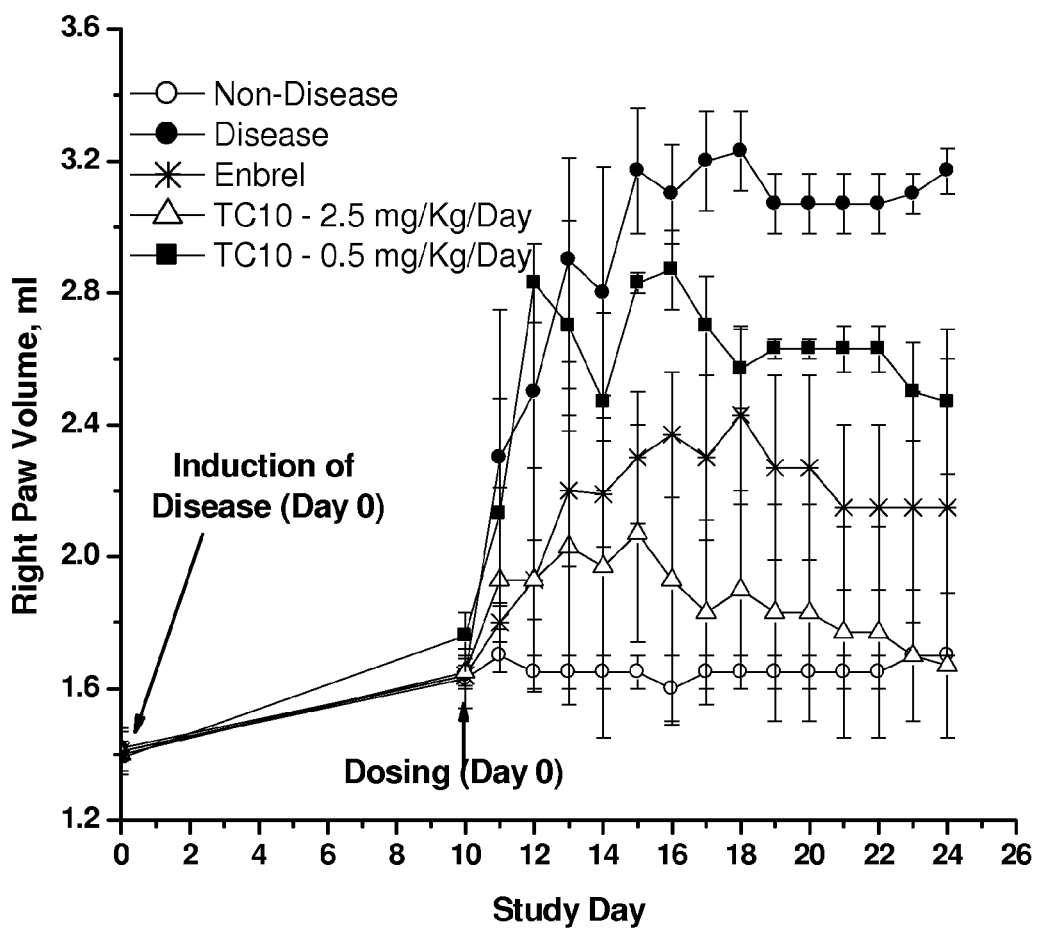
FIG. 27 is a graph showing the effect of TC10 on paw inflammation in a prophylactic model of rat AIA (right paw, IP dosing). The same rats described in FIG. 26 were evaluated for right paw inflammation. The results are similar with maximum inhibition observed at 2.5 mg/kg/day dose bringing inflammation down to the non-disease control level.
Figure 28:
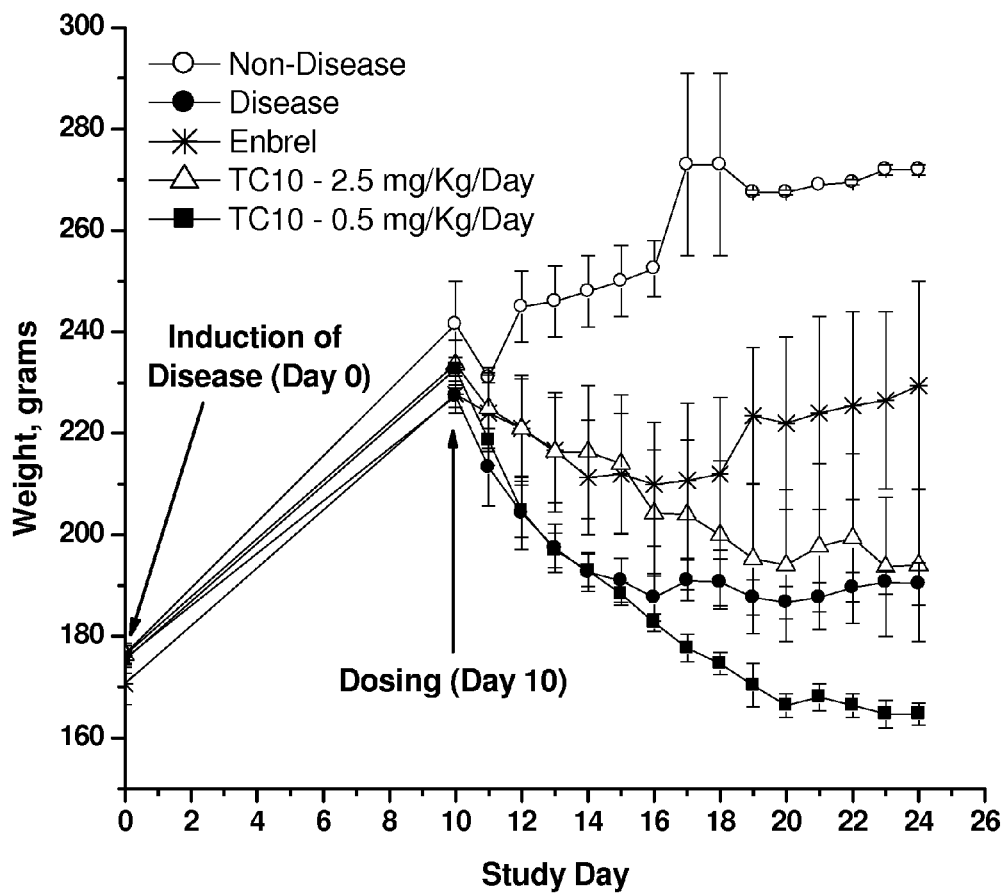
FIG. 28 is a graph showing the effect of TC10 on rat weight in a prophylactic model of rat AIA (IP dosing). The rats described in FIGS. 26-27 were measured for drug effects on weight. Diseased animals tend not to gain weight as demonstrated by FIG. 28. This is compared against the non-disease animals, which do gain weight. Treatment with TC10 does not adversely affect rat weight and gives results comparable to diseased animals. This indicates that TC10 does not adversely affect the rat weight.

As shown in FIGS. 26-27, TC10 at 2.5 mg/kg demonstrated maximal effect better than ENBREL with nearly complete inhibition of paw inflammation. A lower dose of 500 µg/kg/day also reduced paw inflammation. ENBREL was used as a positive control. Animals were weighed at each time point. Weight loss was found to be near negligible compared to disease group as shown in FIG. 28. The large error bars reflect smaller group size.

Figure 29:
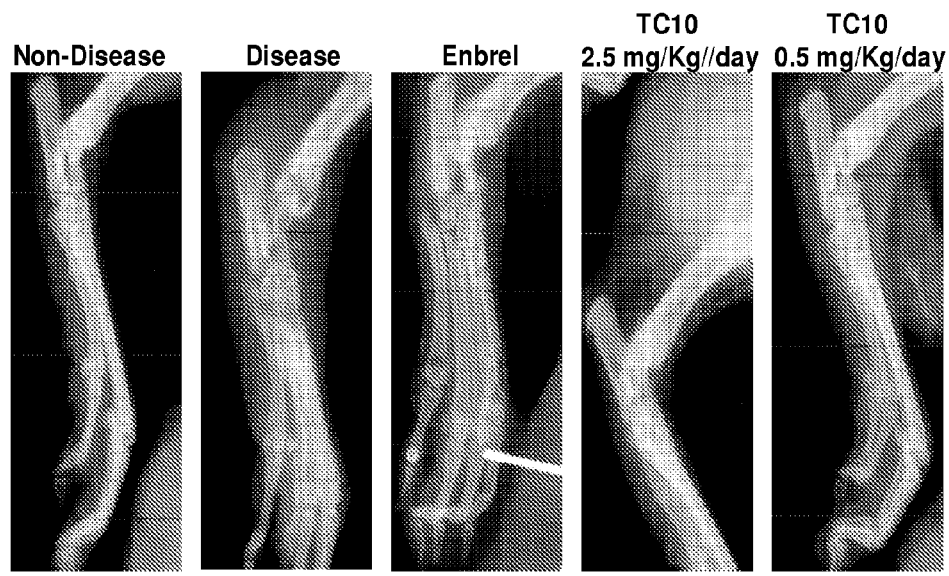
FIG. 29 is a series of radiographs showing the effect of TC10 on joint damage in a prophylactic model of rat AIA (IP dosing). At the termination of the study, the rat limbs were harvested and evaluated for joint damage. The limbs were evaluated for joint damage using x-ray radiography. The radiographs demonstrate that TC10 is able to prevent significant joint damage at both doses 2.5 mg and 0.5 mg compared to the disease control in a dose dependent manner. Both administered doses show significant prevention of joint destruction.
Figure 30:
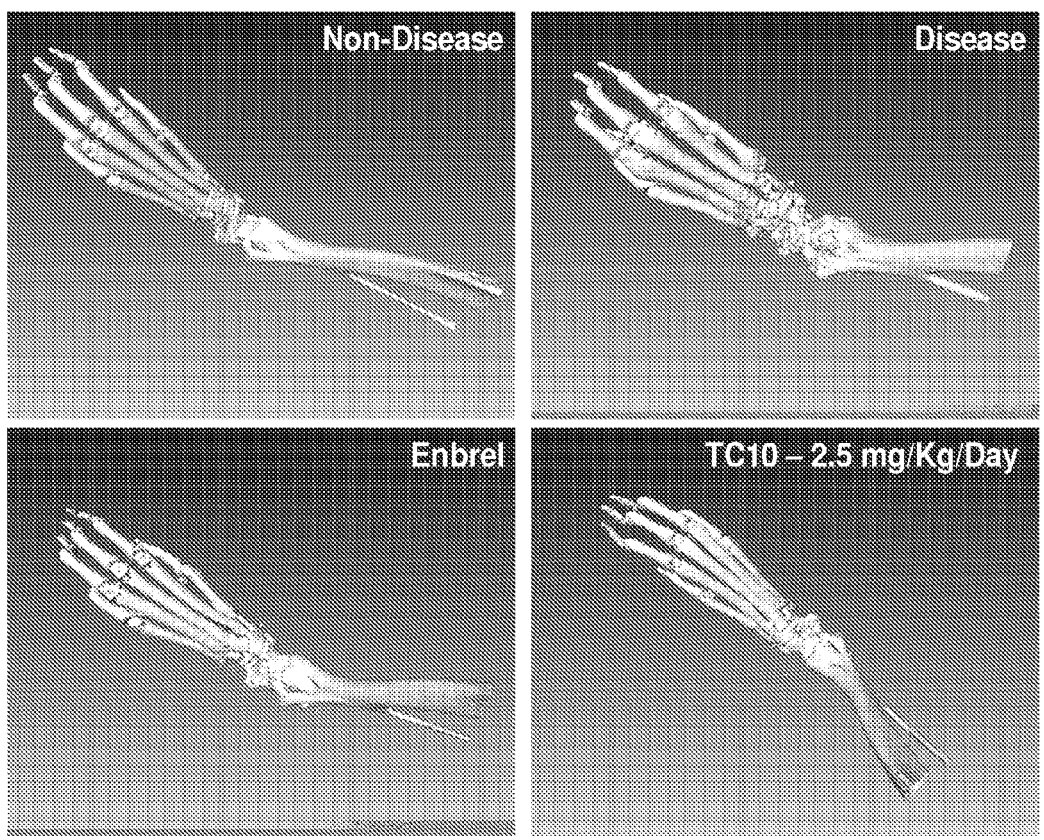
FIG. 30 is a series of CT scans showing the effect of TC10 on joint damage in a prophylactic model of rat AIA (IP dosing). CT scan evaluations were performed at the highest dose. Joint damage was almost completely prevented with no joint damage.

Radiographs shown in FIG. 29 demonstrate that TC10 was effective is preserving the joint damage at both concentrations. Thus, TC10 prevents joint damage similar to those from ENBREL treated group. Disease group shows massive inflammation and joint damage. CT scan of the joints in TC10 treated group at 2.5 mg/kg shows preservation of the joint damage.

EXAMPLE 9

Evaluation of Oral Dosing of TC10 at 2.5, and 0.5 mg/Kg/day IP Dosing in a Female Rat AIA Prophylactic Model Female rats were subjected to arthritis induction as described in Example 1. In this prophylactic model of AIA, TC10 at 2.5, and 0.5 mg/kg/day dosing was given by IP in female rats. The paw volumes were measured every day using plethysmometer. The readouts for each rat were plotted against the study day. ENBREL at 30 mg/kg dose was injected only once a week subcutaneously as a positive control. The animals were dosed for 12 days following which they were euthanized for other readouts such as radiographs and CT scans.

Figure 31:
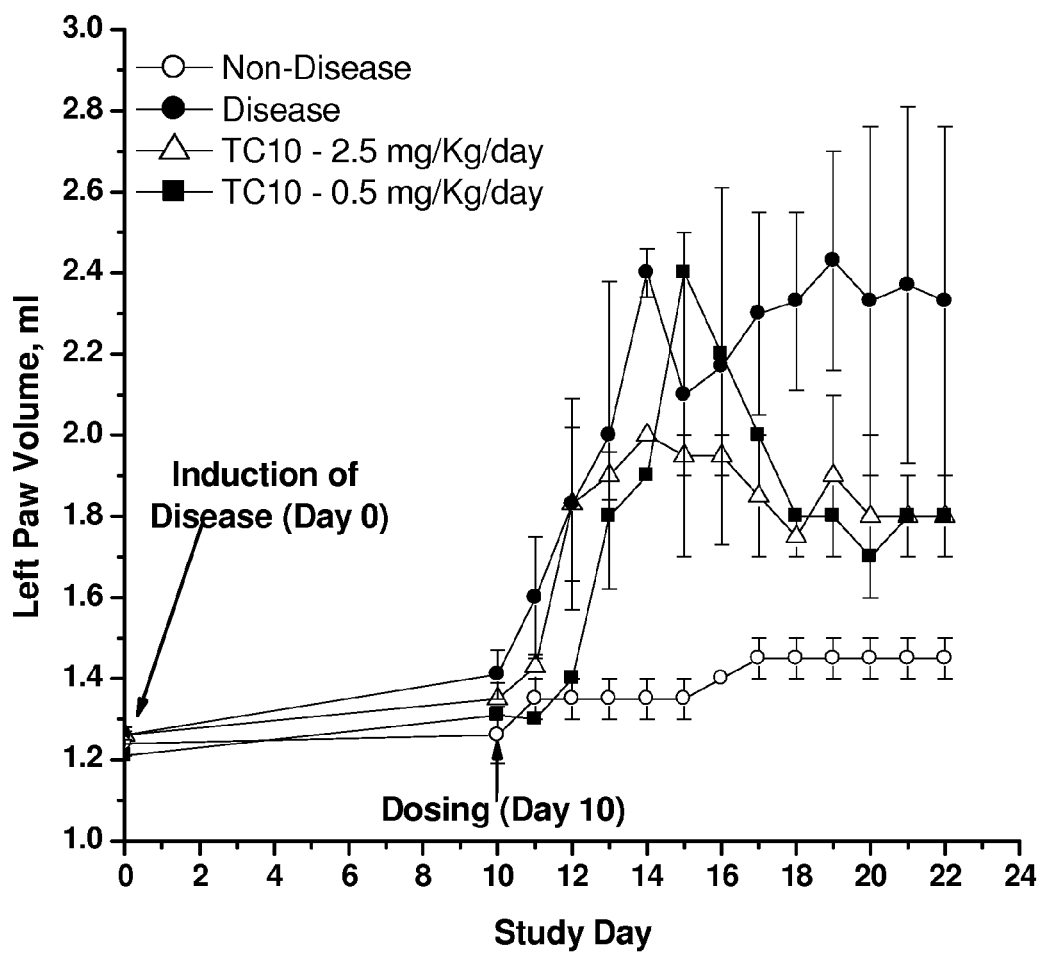
FIG. 31 is a graph showing the effect of TC10 on female rat paw inflammation in a prophylactic model of rat AIA (left paw, IP dosing). TC10 was administered intraperitoneally at different doses in a rat model of adjuvant-induced arthritis to evaluate dose effects of TC10. In this study, female rats were used instead of male rats. The administration was given prophylactically at day 10 to demonstrate prevention of arthritis in rats. These results indicate that TC10 can prevent development and progression of rat adjuvant induced arthritis dose dependently with maximum effect observed at 2.5 mg dosing. The lower dose of 500 μg gave comparable results to the higher dose.
Figure 32:
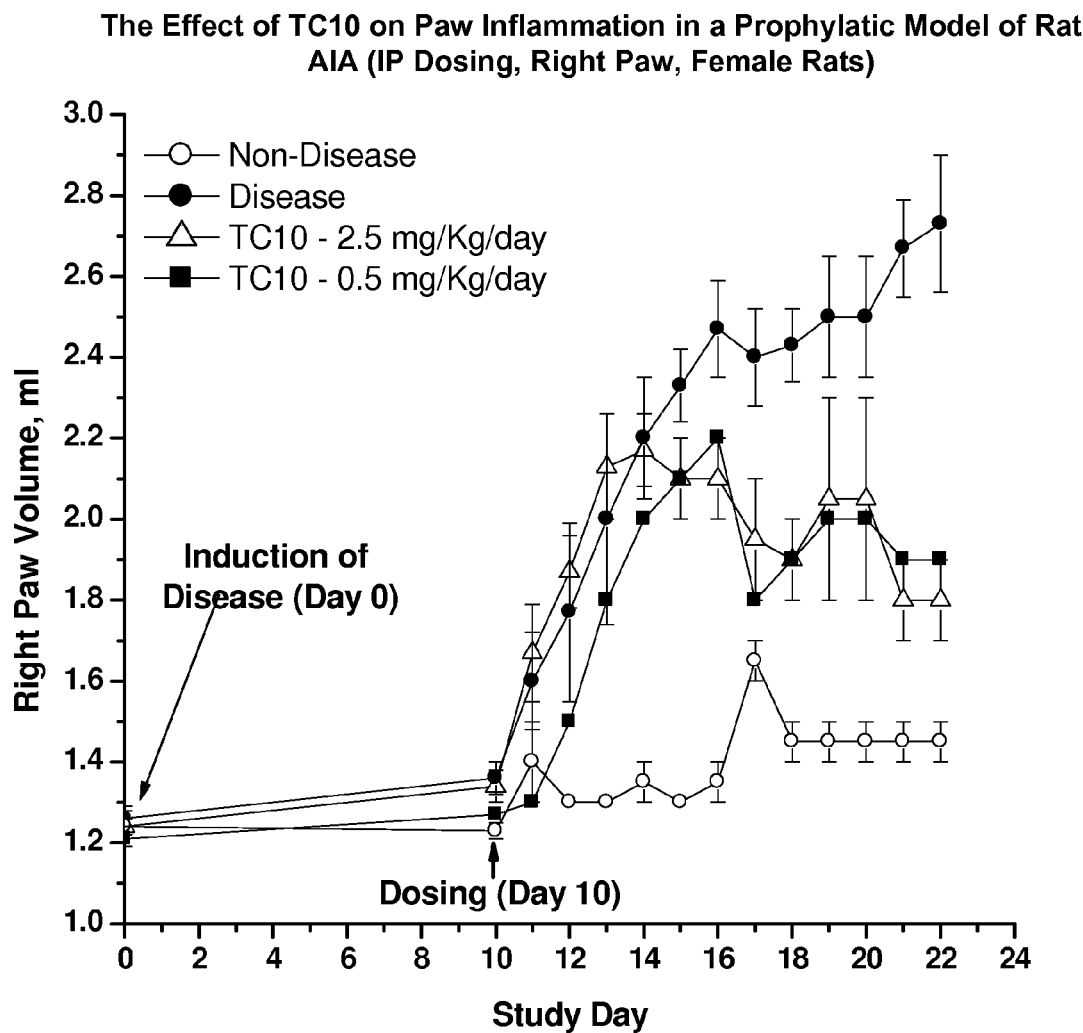
FIG. 32 is a graph showing the effect of TC10 on paw inflammation in a prophylactic model of rat AIA (right paw, IP dosing, female rats). The same rats described in FIG. 31 were evaluated for right paw inflammation. The results are similar with comparable reduction of paw inflammation at both administered doses.
Figure 33:
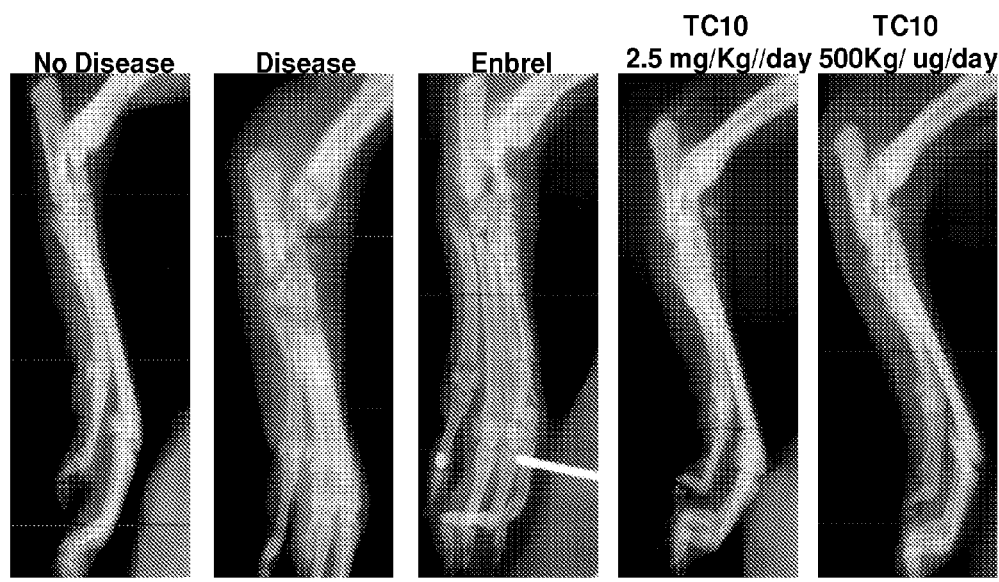
FIG. 33 is a series of radiographs showing the effect of TC10 on joint damage in a prophylactic model of rat AIA (IP dosing). At the termination of the study, the rat limbs were harvested and evaluated for joint damage. The limbs were evaluated for joint damage using x-ray radiography. The radiographs demonstrate that TC10 at 2.5 mg and 0.5 mg/kg is able to prevent significant joint damage compared to the disease control. Both administered doses show significant prevention of joint destruction.

As shown in FIGS. 31-32, TC 10 effect on paw volume was inhibited at both doses. Radiographs shown in FIG. 33 demonstrate that TC10 was effective in preserving the joint damage at both concentrations tested. Thus, TC10 prevents joint damage.

EXAMPLE 10

Evaluation of 5 mg/Kg/day Oral Dosing in a Male Rat AIA Prophylactic Model

Male rats were subjected to arthritis induction as described in Example 1. In this prophylactic model of AIA, TC10 at 5 mg/kg/day dosing was given by oral gavage in male rats. The paw volumes were measured every day using plethysmometer. The readouts for each rat were plotted against the study day. ENBREL at 30 mg/kg dose was injected only once a week subcutaneously as a positive control. The animals were dosed for 14 days following which they were euthanized for other readouts.

Figure 34:
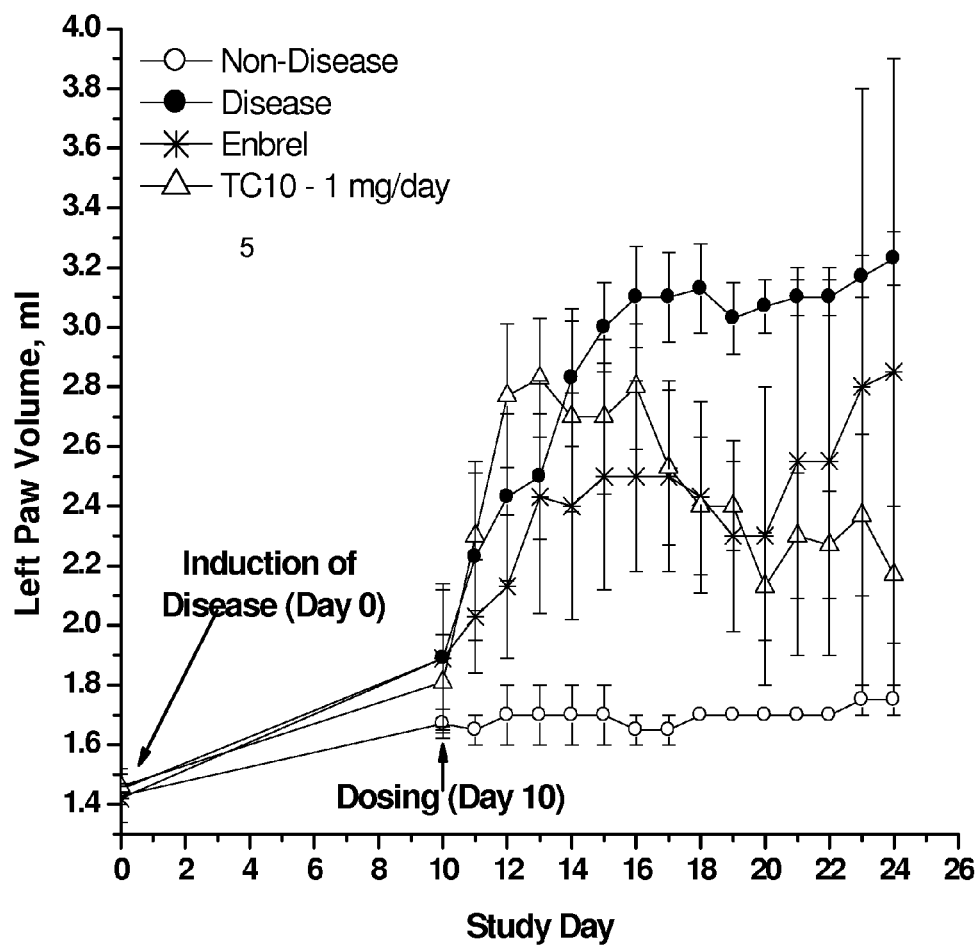
FIG. 34 is a graph showing the effect of TC10 on paw inflammation in a prophylactic model of rat AIA (left paw, oral dosing, male rats). TC10 was administered orally at 5 mg/kg/day in a rat model of adjuvant-induced arthritis to evaluate dose effects of TC10. The administration was given prophylactically at day 10 to male rats to demonstrate prevention of arthritis in rats. These results indicate that TC10 can prevent development and progression of rat adjuvant induced arthritis. These results are not as effective as the IP dosing due to the oral administration. This decrease in potency is due to the limited bioavailability of the compound via oral administration.
Figure 35:
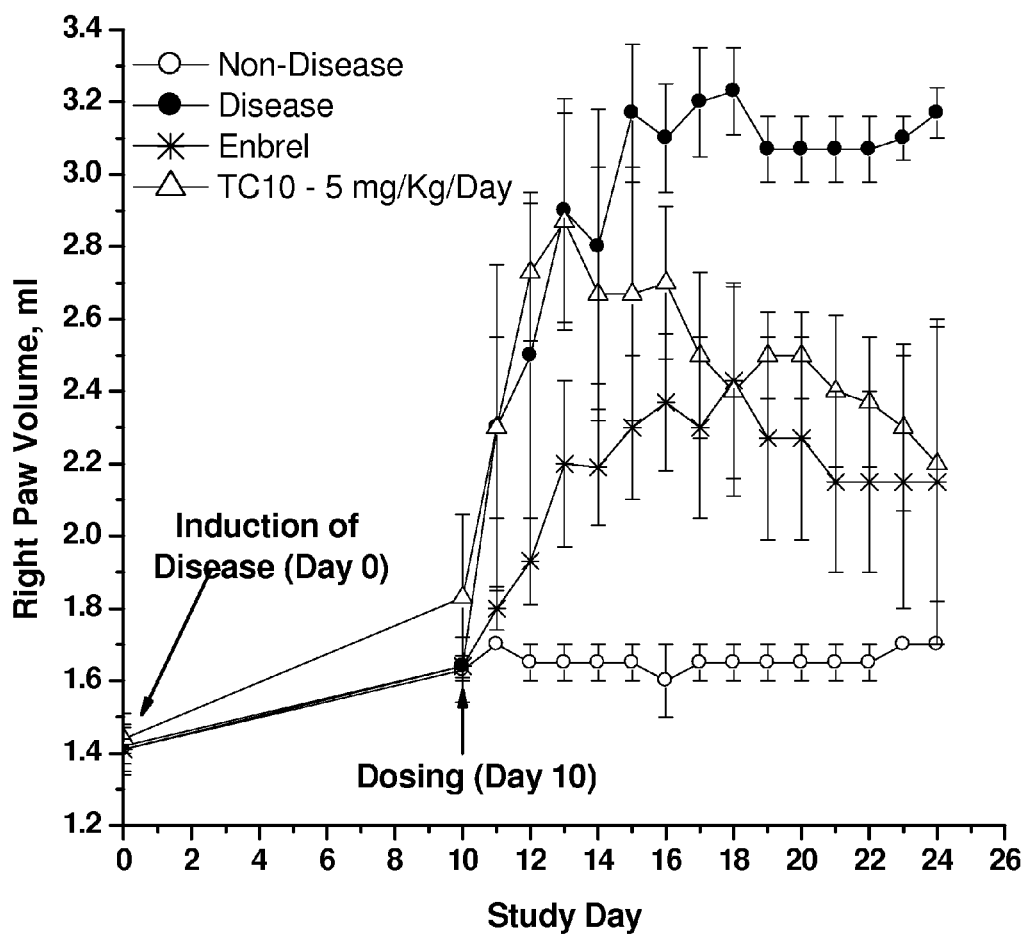
FIG. 35 is a graph showing the effect of TC10 on paw inflammation in a prophylactic model of rat AIA (right paw, oral dosing, male rats). The same rats described in FIG. 34 were evaluated for right paw inflammation. The results are similar to left paw inflammation.
Figure 36:
FIG. 36 is a series of radiographs showing the effect of TC10 on joint damage in a prophylactic model of rat AIA (oral dosing, male rats). At the termination of the study, the rat limbs were harvested and evaluated for joint damage. The limbs were evaluated for joint damage using x-ray radiography. The radiographs demonstrate that TC10 is able to prevent significant joint damage compared to the disease control at 5 mg/kg dose tested.
Figure 37:
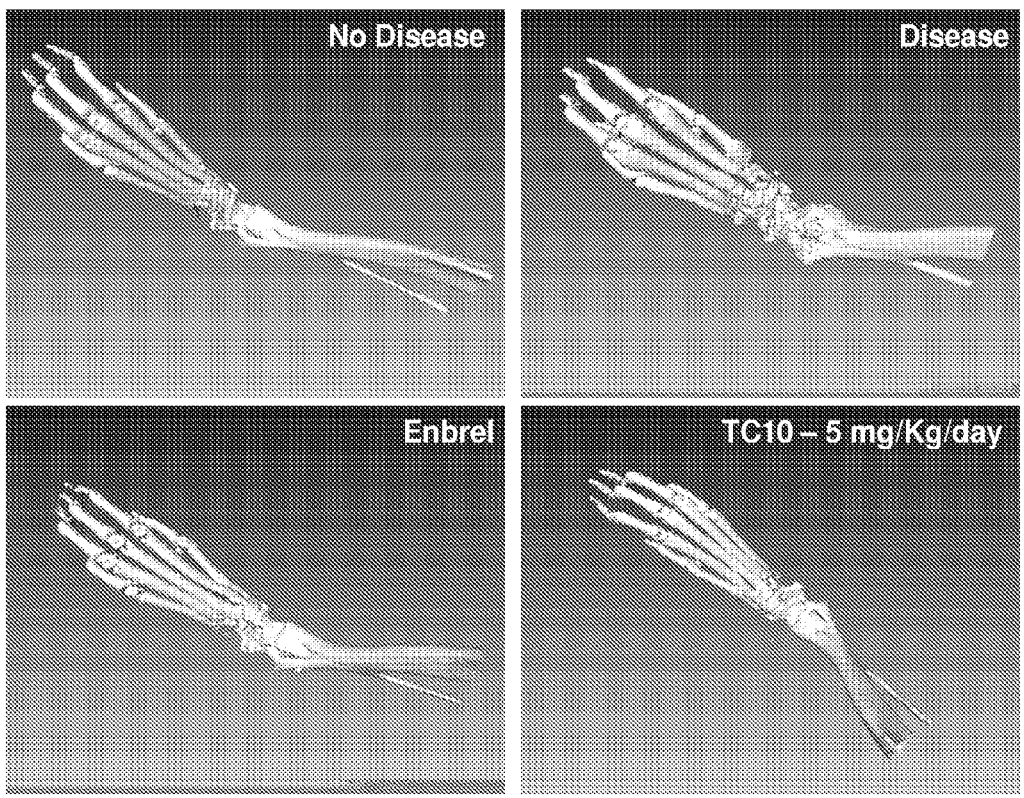
FIG. 37 is a series of CT scans showing the effect of TC10 on joint damage in a prophylactic model of rat AIA (IP dosing, CT scans). The same limbs described in FIG. 36 were evaluated for joint damage using CT scanning. The benefit of CT scanning is that it provides clearer imaging of joint structure than the radiograph. As observed in the figure there is significant reduction in bone damage in treated animals compared to diseased animals. CT scanning of the TC10 group demonstrated near complete prevention of joint destruction at 5 mg/kg/day compared to the diseased control.

As shown in FIGS. 34-35, TC 10 inhibited paw inflammation to ENBREL controls. FIG. 36 shows that TC10 effectively preserves the joint damage. Similar results were obtained from the CT scan of the joint shown in FIG. 37.

Figure 38:
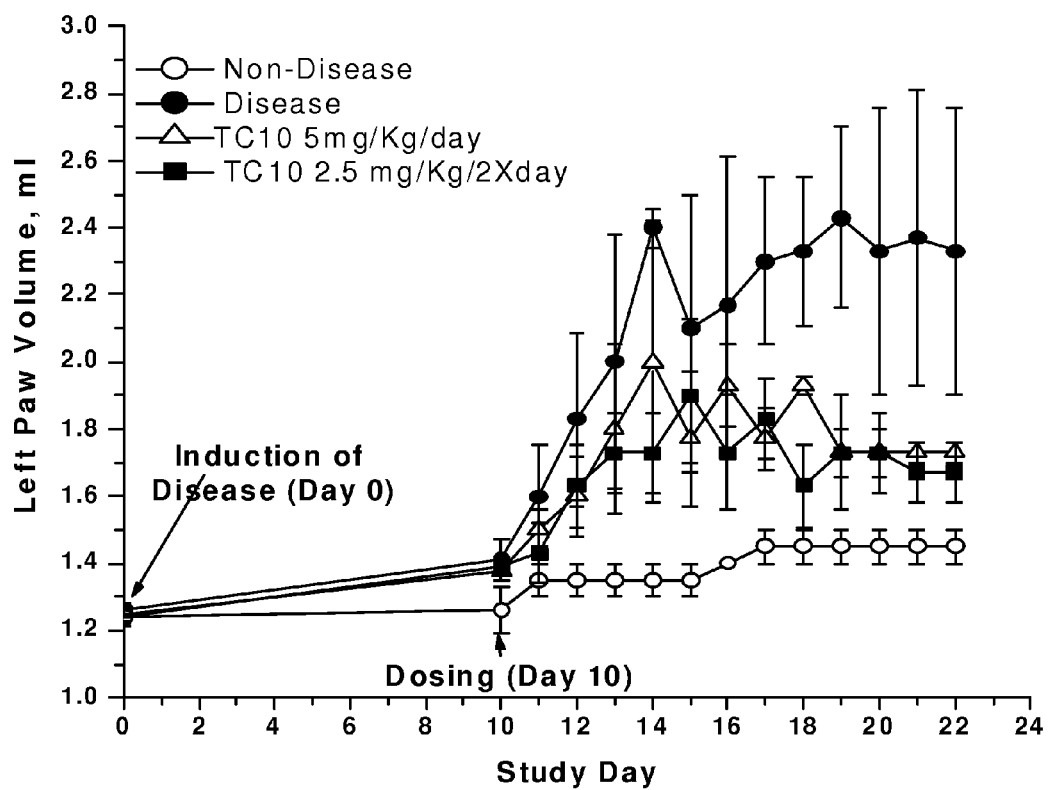
FIG. 38 is a graph showing the effect of TC10 on paw inflammation in a prophylactic model of rat AIA (left paw, oral dosing, female rats). TC10 was administered orally at 5 mg and 2.5 mg/kg/day in a rat model of adjuvant-induced arthritis to evaluate dose effects of TC10. The study is the same as the oral administration in male rats with the only difference being that female rats were used and the dosing was 1 mg/rat/day and 500 µg/rat twice daily. Both dosing of TC10 showed significant reduction in paw inflammation.
Figure 39:
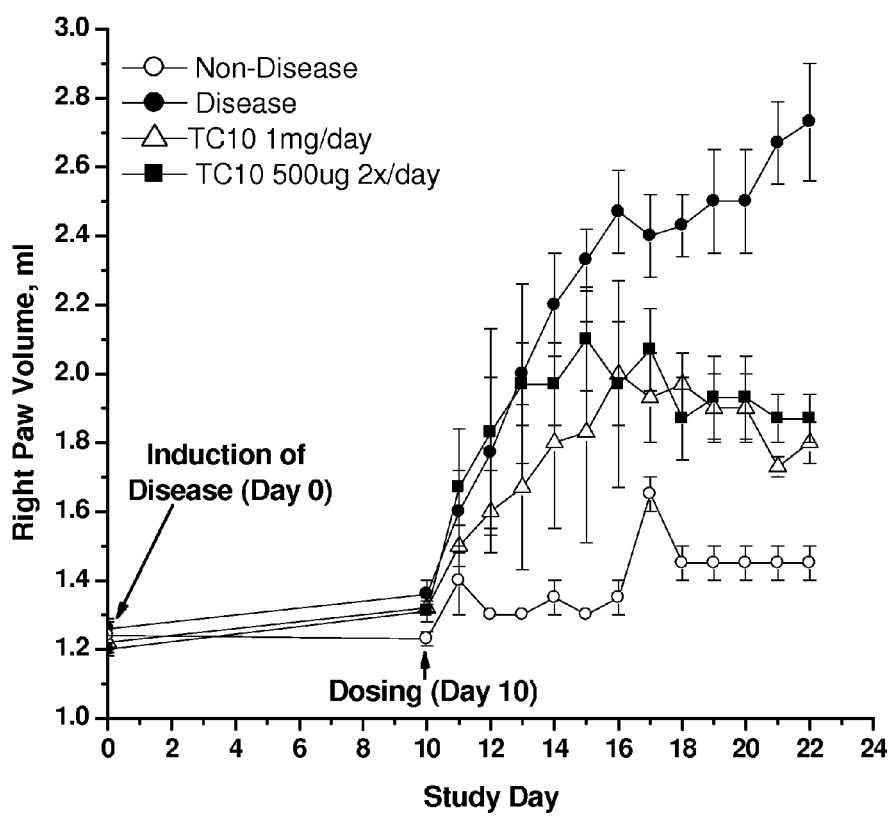
FIG. 39 is a graph showing the effect of TC10 on paw inflammation in a prophylactic model of rat AIA (right paw, oral dosing, female rats). The same rats described in FIG. 38 were evaluated for right paw inflammation. The results are similar to left paw inflammation.
Figure 40:
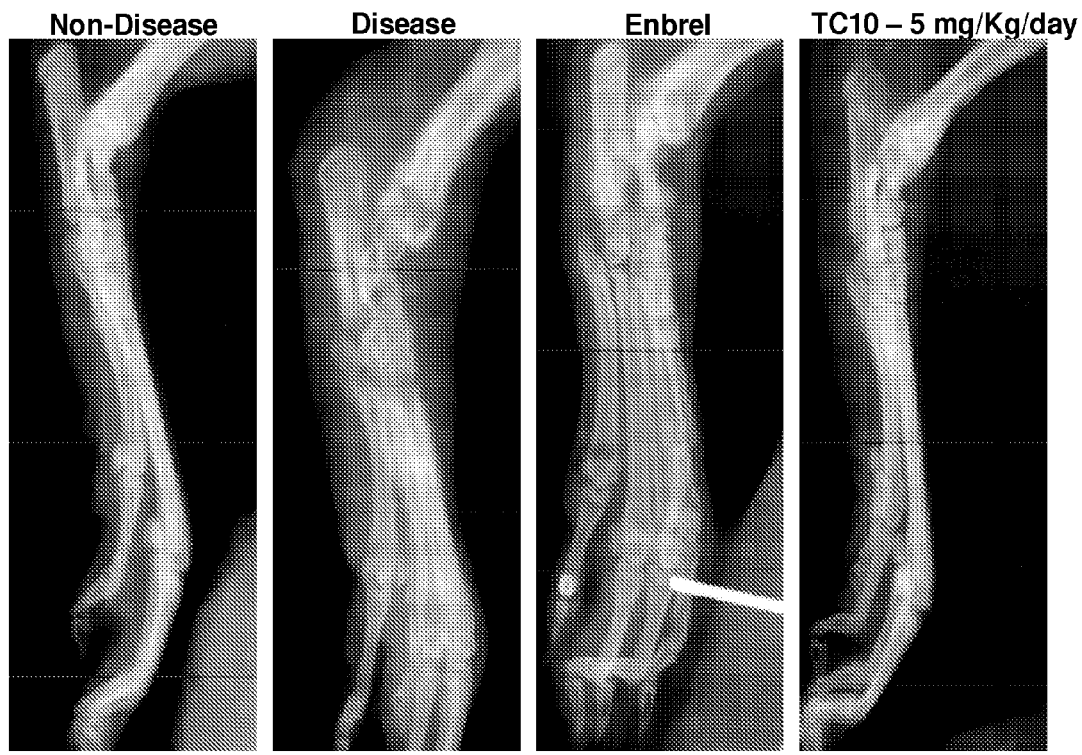
FIG. 40 is a series of radiographs showing the effect of TC10 on joint damage in a prophylactic model of rat AIA (oral dosing, male rats). At the termination of the study, the rat limbs were harvested and evaluated for joint damage. The limbs were evaluated for joint damage using x-ray radiography. Radiography was done at the 5 mg/kg/day dose.

When TC10 was tested in female rats, both 5 and 2.5 mg/kg dosing prevented paw inflammation (FIGS. 38-39). Radiographic images (FIG. 40) suggests that TC10 is effective in female rates in preserving joint damage.

EXAMPLE 11

Evaluation of TC10 in a Mouse Collagen-Induced Arthritis Model

Male DBA/J1 mice (7-9 weeks old from Jackson Labs, Bar Harbor, Me., USA) were used. The CIA study using mice of same age, strain and source was performed at Boulder Bio-PATH Inc as described below. Male DBA/J1 mice were shaved at the base of the tail and injected with 0.1 ml emulsion consisting of a 1 to 1 (1 mg/1 mg) mixture of type II chicken collagen with *Mycobacterium butyricum* (Difco) as an adjuvant. Three weeks later, the mice were boosted with another 0.1 ml injection of emulsion at the base of the tail to induce disease. Dosing started at day 18 while the last boost to induce the disease was at day 21. The mice were scored in a blinded manner twice weekly for 3 weeks for signs of arthritis in each paw according to the following scale: clinical signs were evaluated using the following scale: 0=normal; 1=one joint affected or mild diffuse erythema and swelling; 2=two joints affected or mild diffuse erythema and swelling; 3=three joints affected or mild diffuse erythema and swelling; 4=four joint affected or marked diffuse erythema and swelling; and 5=severe erythema and severe swelling. Upon study completion (day 28), mice were killed with $CO_2$.

Figure 41:
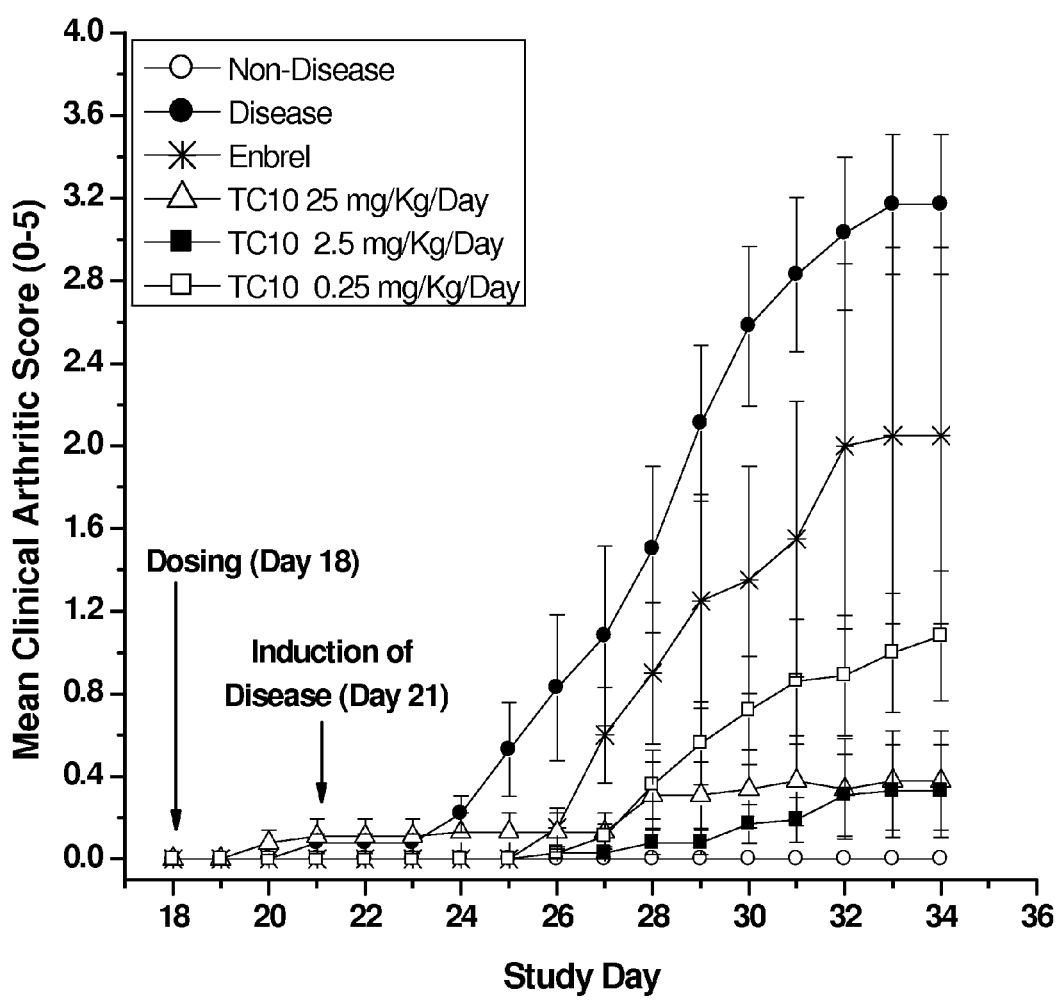
FIG. 41 is a graph showing the effect of TC10 on paw inflammation in prophylactic model of mouse CIA (IP dosing). TC10 was evaluated in a mouse model of collagen-induced arthritis at 25 mg, 2.5 mg, and 0.25 mg per kg dose in mouse CIA model of arthritis. This model is another standard model of arthritis for drug evaluation. The effect of arthritic development is measured based on clinical scoring of the paws. TC10 was administered at different doses in this study and were found to have significant prevention of arthritis with inhibition greater than ENBREL at all tested doses.

Three different doses were administered IP (25, 2.5, and 0.25 mg/kg). As shown in FIG. 41, there were 9 animals per group with 6 in control disease and non-disease groups. All three doses inhibited clinical signs of the disease. Compared to the ENBREL group, TC10 was found to be effective at all three doses.

EXAMPLE 12

Evaluation of TC10 (NM2026), Tamoxifen (NM5493), Clomiphene (NM4994), Estradiol (NM6043), Fulvestrant (NM7312), and NM6647 at 5 mg/Kg/day Dosing in a Male Rat AIA Prophylactic Model Male rats were subjected to arthritis induction as described in Example 1. In this prophylactic model of AIA, TC10 (NM2026), Tamoxifen (NM5493), Clomiphene (NM4994), Estradiol (NM6043), Fulvestrant (NM7312), and NM6647 at, respectively, 5 mg/Kg/day dosing was injected IP in male rats. The paw volumes were measured every day using plethysmometer. The readouts for each rat were plotted against the study day. ENBREL at 30 mg/kg dose was injected only once a week subcutaneously. The animals were dosed for 14 days following which they were euthanized for other readouts.

Figure 42:
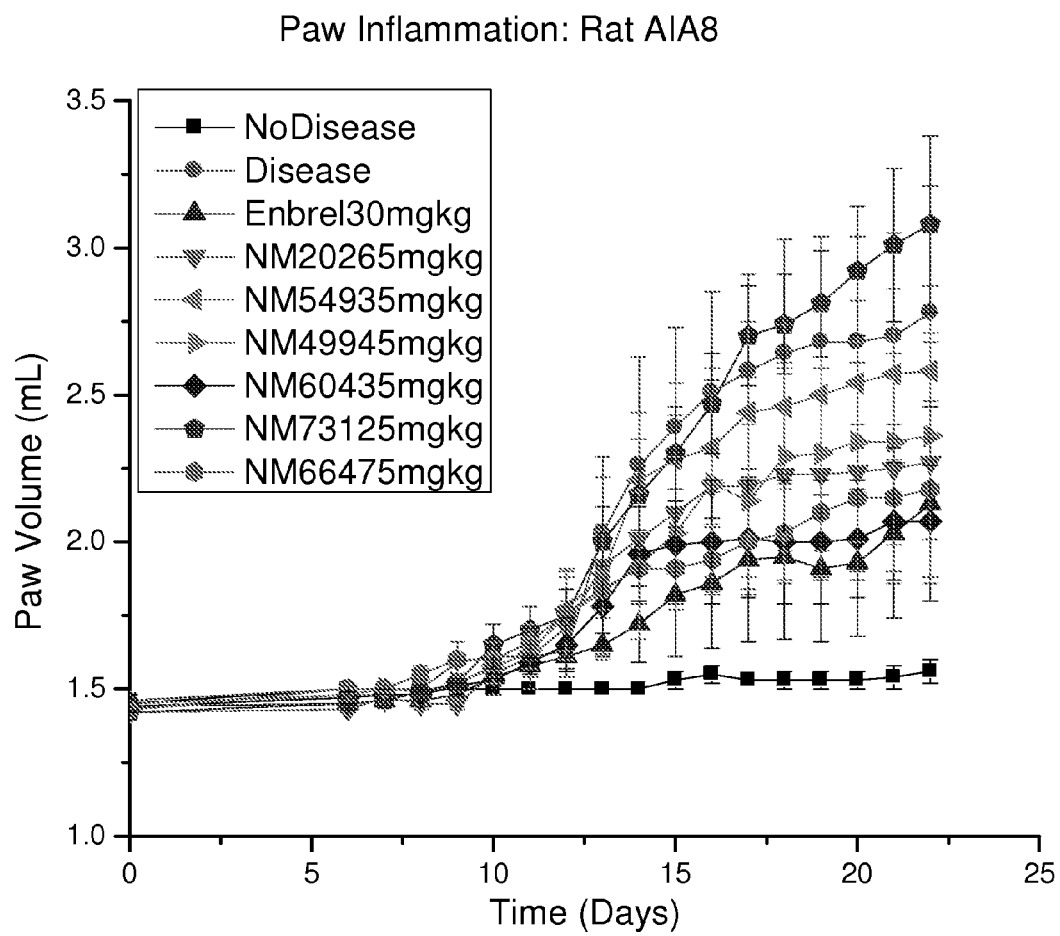
FIG. 42 is a graph showing the effect of TC10 (NM2026), Tamoxifen (NM5493), Clomiphene (NM4994), Estradiol (NM6043), Fulvestrant (NM7312), and NM6647 on right paw inflammation in a prophylactic model of rat AIA. at 5 mg/Kg/day Dosing in a Male Rat AIA Prophylactic Model. TC10 (NM2026), Tamoxifen (NM5493), Clomiphene (NM4994), Estradiol (NM6043), Fulvestrant (NM7312), and NM6647 were administered intraperitoneally at 5 mg/kg/day. The administration was given prophylactically at day 10 to demonstrate prevention of arthritis in rats. Development of arthritis usually takes 14 days to progress.

As shown in FIG. 42, TC10 and Tamoxifen, estrogen receptor agonists, reduced paw inflammation to control levels similar to those observed for ENBREL. ENBREL was used as a positive control. Animals were also weighed at each time points. Weight loss was found to be near negligible compared to control ENBREL group. The large error bars reflect smaller group size.

EXAMPLE 13

Evaluation of TC10 (NM2026) at 5 mg/Kg/day Dosing in a Male Rat AIA Prophylactic Model Male rats were subjected to arthritis induction as described in Example 1. In this prophylactic model of AIA, TC10 (NM2026) at 5 mg/Kg/day dosing was injected IP in male rats. The paw volumes were measured every day using plethysmometer. The readouts for each rat were plotted against the study day. ENBREL at 30 mg/kg dose was injected only once a week subcutaneously. The animals were dosed for 14 days following which they were euthanized for other readouts.

Figure 43:
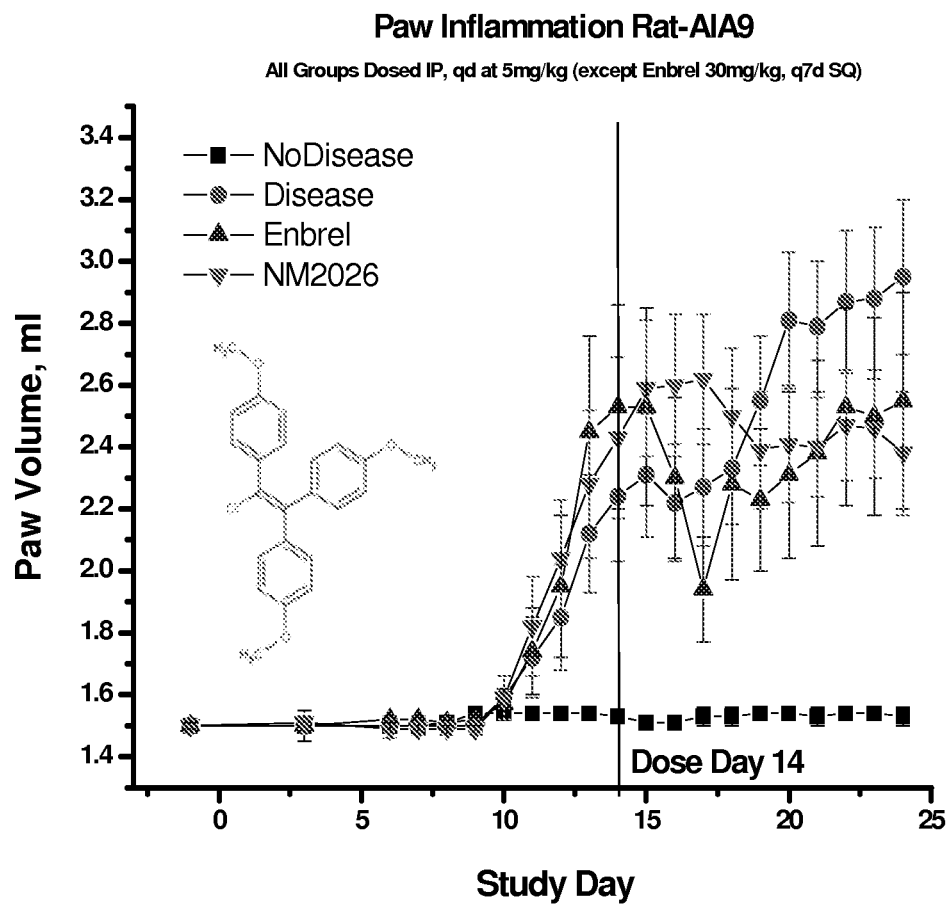
FIG. 43 is a graph showing the effect of NM2026 on paw inflammation in a prophylactic model of rat AIA (right paw, IP dosing). NM2026 was administered intraperitoneally at 5 mg/kg/day in a rat model of adjuvant-induced arthritis similar to as described for FIG. 1. The same rats were evaluated for right paw inflammation. NM2026 was able to inhibit paw inflammation similar to the effects of ENBREL.

As shown in FIG. 43, TC10 reduced paw inflammation to control levels similar to those observed for ENBREL. ENBREL was used as a positive control Animals were also weighed at each time points. Weight loss was found to be near negligible compared to control ENBREL group. The large error bars reflect smaller group size.

EXAMPLE 14

Evaluation of TC10 (NM2026) and NM9630 at 5 mg/Kg/day Dosing in a Male Rat AIA Prophylactic Model Male rats were subjected to arthritis induction as described in Example 1. In this prophylactic model of AIA, TC10 (NM2026) and NM9630 (structure shown) at 5 mg/Kg/day dosing was injected IP in male rats. The paw volumes were measured every day using plethysmometer. The readouts for each rat were plotted against the study day. The animals were dosed for 14 days following which they were euthanized for other readouts.

Figure 44:
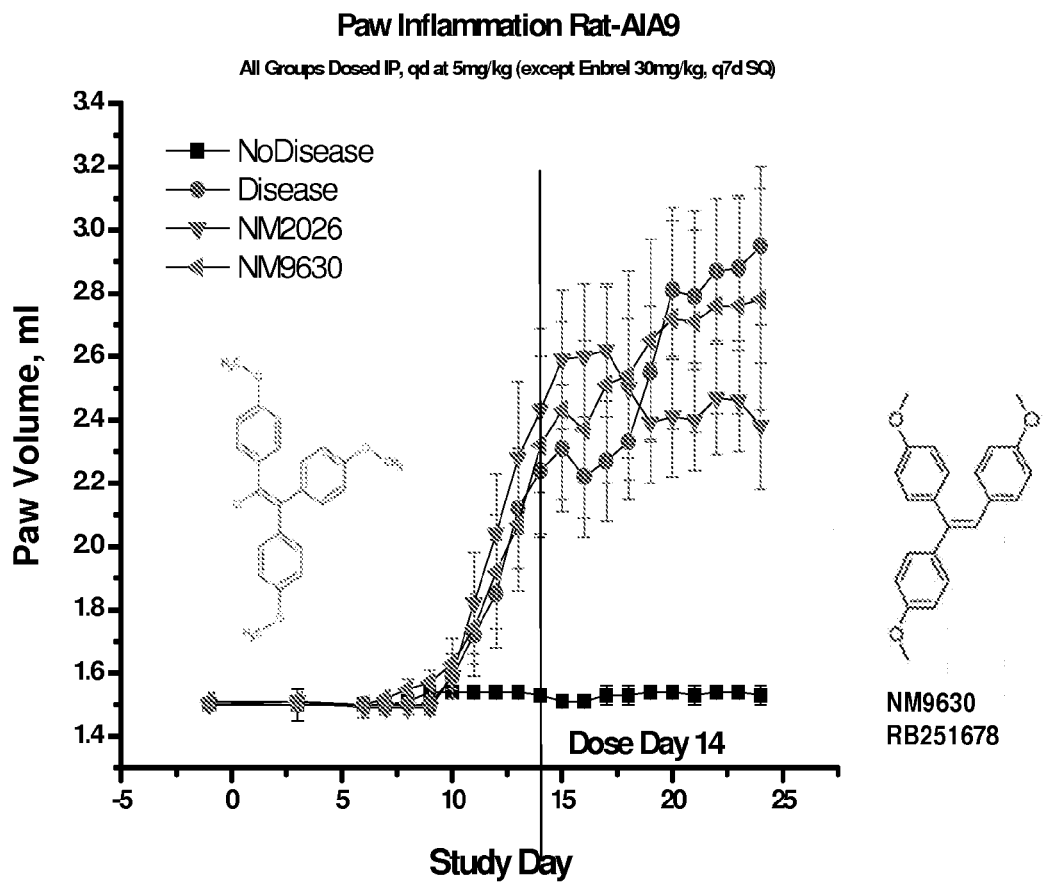
FIG. 44 is a graph showing the effect of NM9630 on paw inflammation in a prophylactic model of rat AIA (right paw, IP dosing). NM9630 was administered intraperitoneally at 5 mg/kg/day in a rat model of adjuvant-induced arthritis similar to as described for FIG. 43. The same rats were evaluated for right paw inflammation. NM9630 was able to inhibit paw inflammation similar to the effects of NM2026.

As shown in FIG. 44, TC10 and NM9630 reduced paw inflammation Animals were also weighed at each time points.

EXAMPLE 15

Evaluation of TC10 (NM2026) and NM9632 at 5 mg/Kg/day Dosing in a Male Rat AIA Prophylactic Model Male rats were subjected to arthritis induction as described in Example 1. In this prophylactic model of AIA, TC10 (NM2026) and NM9632 (structure shown) at 5 mg/Kg/day dosing was injected IP in male rats. The paw volumes were measured every day using plethysmometer. The readouts for each rat were plotted against the study day. The animals were dosed for 14 days following which they were euthanized for other readouts.

Figure 45:
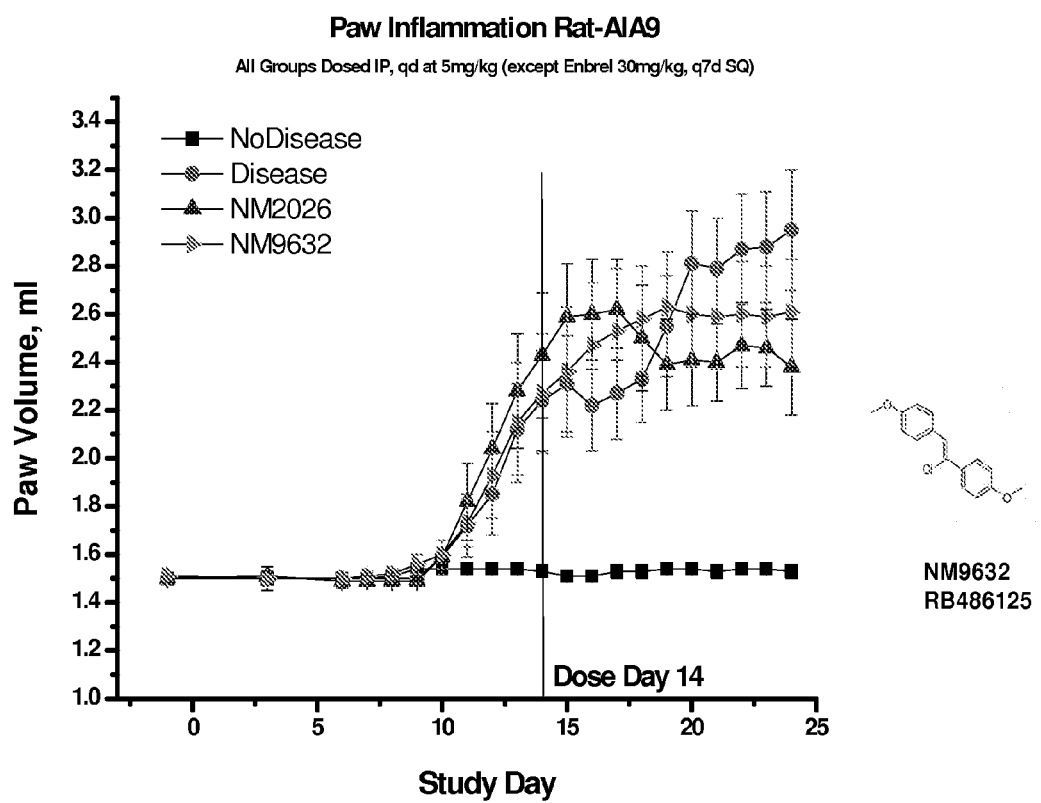
FIG. 45 is a graph showing the effect of NM9632 on paw inflammation in a prophylactic model of rat AIA (right paw, IP dosing). NM9632 was administered intraperitoneally at 5 mg/kg/day in a rat model of adjuvant-induced arthritis similar to as described for FIG. 43. The same rats were evaluated for right paw inflammation. NM9632 was able to inhibit paw inflammation similar to the effects of NM2026.

As shown in FIG. 45, NM9632 reduced paw inflammation to control levels similar to those observed for TC10. TC10 was used as a positive control Animals were also weighed at each time points. Weight loss was found to be near negligible compared to control TC10 group. The large error bars reflect smaller group size.

EXAMPLE 16

Evaluation of TC10 (NM2026) and NM9636 at 5 mg/Kg/day Dosing in a Male Rat AIA Prophylactic Model Male rats were subjected to arthritis induction as described in Example 1. In this prophylactic model of AIA, TC10 (NM2026) and NM9636 (structure shown) at 5 mg/Kg/day dosing was injected IP in male rats. The paw volumes were measured every day using plethysmometer. The readouts for each rat were plotted against the study day. The animals were dosed for 14 days following which they were euthanized for other readouts.

Figure 46:
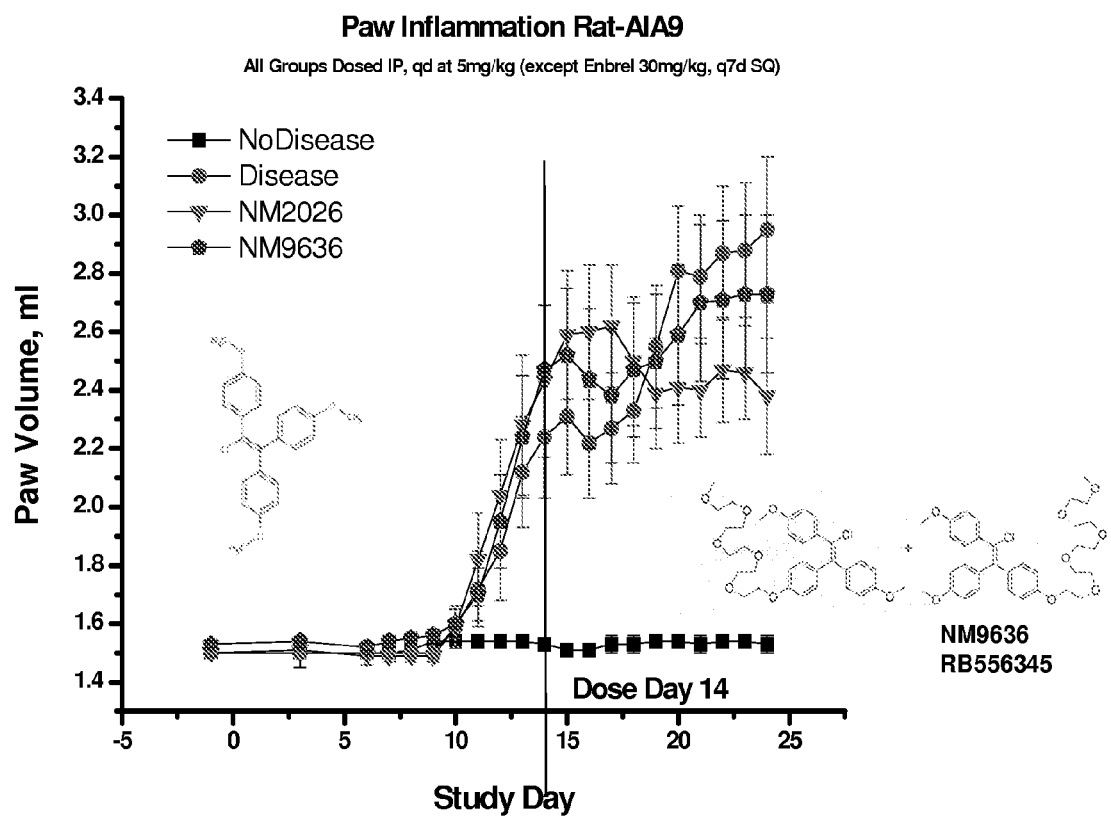
FIG. 46 is a graph showing the effect of NM9636 on paw inflammation in a prophylactic model of rat AIA (right paw, IP dosing). NM9636 was administered intraperitoneally at 5 mg/kg/day in a rat model of adjuvant-induced arthritis similar to as described for FIG. 43. The same rats were evaluated for right paw inflammation. NM9636 was able to inhibit paw inflammation similar to the effects of NM2026.

As shown in FIG. 46, NM9636 reduced paw inflammation. The large error bars reflect smaller group size.

From the above description of the invention, those skilled in the art will perceive improvements, changes and modifications. Such improvements, changes and modifications within the skill of the art are intended to be covered by the appended claims. It will be appreciated that references, patents, and publication recited in the application are herein incorporated by reference in their entirety.

Having described the invention, the following is claimed:

1. A method for treating arthritis in a subject consisting essentially of:
systemically administering to the subject a therapeutically effective amount of:
at least one imidazole having a formula of:

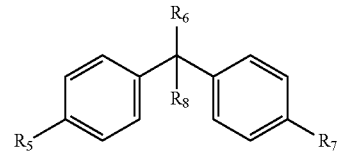

wherein $R_5$, $R_6$, $R_7$, and $R_8$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halogen, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (CO)—NH($C_1$-$C_{24}$ alkyl)), di-($C_1$-$C_{24}$ substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof or a pharmaceutically acceptable salt thereof, and wherein at least one of $R_6$ or $R_8$ is an imidazole or a substituted imidazole.

2. The method of claim 1, wherein the imidazole is 1-[phenyl(4-phenylphenyl)methyl]-1H-imidazole or a pharmaceutically acceptable salt thereof.

3. The method of claim 1, wherein the arthritis is selected from the group consisting of septic arthritis, rheumatoid arthritis and osteoarthritis.

4. A method for treating rheumatoid arthritis in a subject, the method consisting essentially of: administering to the subject a therapeutically effective amounts of an agent comprising at least one imidazole having a formula of:

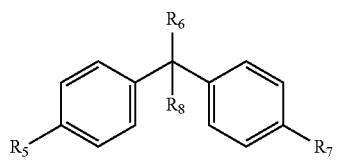

wherein $R_5$, $R_6$, $R_7$, and $R_8$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halogen, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl (—CO-alkyl), $C_6$-$C_{20}$ arylcarbonyl (—CO-aryl), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N+C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl (—S-alkyl), arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof or a pharmaceutically acceptable salt thereof, and wherein at least one of $R_6$ or $R_8$ is an imidazole or a substituted imidazole.

5. The method of claim 4, wherein the agent is 1-[phenyl(4-phenylphenyl)methyl]-1H-imidazole or a pharmaceutically acceptable salt thereof.

6. The method of claim 1, wherein the imidazole is administered through an intravenous or oral route.

7. The method of claim 1, wherein the imidazole is administered in a dose of about 1 mg to about 1000 mg per day.

8. The method of claim 4, wherein the agent is administered through a route of administration selected from the group comprising of oral, intraperitoneal, parenteral, subcutaneous, transdermal, sublingual, nasal, opthalmic, intramuscular, pulmonary, topical, intraarticular, rectal and vaginal routes.

9. The method of claim 8, wherein the agent is administered systemically.

10. The method of claim 9, wherein the agent is administered through an intravenous or oral route.

11. The method of claim 8, wherein the agent is administered in a dose of about 1 mg to about 1000 mg.

* * * * *